(12) United States Patent
Luthringer

(10) Patent No.: US 11,083,723 B2
(45) Date of Patent: Aug. 10, 2021

(54) USE OF ROLUPERIDONE TO TREAT NEGATIVE SYMPTOMS AND DISORDERS, INCREASE NEUROPLASTICITY, AND PROMOTE NEUROPROTECTION

(71) Applicant: Minerva Neurosciences, Inc., Waltham, MA (US)

(72) Inventor: Remy Henri Luthringer, Geneva (CH)

(73) Assignee: Minerva Neurosciences, Inc., Waltham, MA (US)

( * ) Notice: Subject to any disclaimer, the term of this patent is extended or adjusted under 35 U.S.C. 154(b) by 0 days.

(21) Appl. No.: 16/547,164

(22) Filed: Aug. 21, 2019

(65) Prior Publication Data

US 2020/0061046 A1 Feb. 27, 2020

Related U.S. Application Data

(60) Provisional application No. 62/831,535, filed on Apr. 9, 2019, provisional application No. 62/720,667, filed on Aug. 21, 2018.

(51) Int. Cl.
*A61K 31/454* (2006.01)
*A61P 25/28* (2006.01)

(52) U.S. Cl.
CPC ............ *A61K 31/454* (2013.01); *A61P 25/28* (2018.01)

(58) Field of Classification Search
CPC .................................................. A61K 31/454
See application file for complete search history.

(56) References Cited

U.S. PATENT DOCUMENTS

| | | | |
|---|---|---|---|
| 4,522,811 A | 6/1985 | Eppstein et al. | |
| 4,908,369 A | 3/1990 | Schechter et al. | |
| 9,458,130 B2 * | 10/2016 | Luthringer | C07D 401/06 |
| 9,730,920 B2 * | 8/2017 | Luthringer | A61K 31/454 |
| 9,732,059 B2 * | 8/2017 | Luthringer | H04L 5/0016 |
| 10,258,614 B2 * | 4/2019 | Luthringer | A61K 9/2054 |
| 10,286,032 B2 | 5/2019 | Adini et al. | |
| 2003/0212094 A1 | 11/2003 | Yamabe et al. | |
| 2010/0029726 A1 | 2/2010 | Blackaby et al. | |
| 2013/0273156 A1 | 10/2013 | Loeches Blas et al. | |
| 2013/0274289 A1 | 10/2013 | Luthringer et al. | |
| 2013/0274290 A1 | 10/2013 | Luthringer et al. | |
| 2014/0018348 A1 | 1/2014 | Javitt | |
| 2016/0354357 A1 | 12/2016 | Luthringer et al. | |
| 2018/0155318 A1 | 6/2018 | Luthringer et al. | |
| 2019/0038561 A1 | 2/2019 | Saoud et al. | |
| 2019/0216793 A1 * | 7/2019 | Luthringer | A61P 25/18 |
| 2020/0022968 A1 * | 1/2020 | Luthringer | A61P 25/24 |

FOREIGN PATENT DOCUMENTS

| | | | |
|---|---|---|---|
| GB | 2462611 A | 2/2000 | |
| WO | WO 91/06297 A1 | 5/1991 | |
| WO | WO-2012012542 A1 * | 1/2012 | H04L 5/005 |
| WO | WO 2012/123922 A1 | 9/2012 | |
| WO | WO 2014/011590 A2 | 1/2014 | |
| WO | WO 2015/191554 A1 | 12/2015 | |
| WO | WO-2017205393 A1 * | 11/2017 | A61K 31/454 |

OTHER PUBLICATIONS

Addington et al., "Assessing Depression in Schizophrenia: The Calgary Depression Scale," British Journal of Psychiatry (1993), 163 (suppl. 22), 39-44.
Alon, A. et al, "Identification of the gene that codes for the $\sigma_2$ receptor," PNAS, Jul. 3, 2017;114(27):7160-7165.
Ameen et al., "Negative Symptoms in the Remission Phase of Bipolar Disorder," German Journal of Psychiatry, 2007; 10: 1-7.
An energy nerve magazine, 2009, 111 (3), p. 288-292 (English translation of Japanese Office Action for Japanese Application No. 2017-225061 attached).
Arnt, J. et al. "Do Novel Antipsychotics Have Similar Pharmacological Characteristics? A Review of the Evidence", Neuropsychopharmacology, 1998, vol. 18, No. 2, p. 63-101.
Balbach, S. et al, "Pharmaceutical evaluation of early development candidates: 'The 100 mg-approach'," International Journal of Pharmaceutics, (2004), 275, pp. 1-12.
Balkowiec and Katz, "Cellular Mechanisms Regulating Activity-Dependent Release of Native Brain-Derived Neurotrophic Factor from Hippocampal Neurons," J. Neuroscience (2002) 22(23):10399-10407.
Barrantes-Vidal et al., "Psychopathology, social adjustment and personality correlates of schizotypy clusters in a large nonclinical sample," Schizophrenia Research 122 (2010) 219-225.
Bastiaansen et al., "Diagnosing Autism Spectrum Disorders in Adults: the Use of Autism Diagnostic Observation Schedule (ADOS) Module 4," J. Autism Dev. Disord. (2011), 41:1256-1266.
Bastin, R.J et al, "Salt Selection and Optimisation Procedures for Pharmaceutical New Chemical Entities," Organic Process & Development, 2000, 4(5), pp. 427-435.

(Continued)

*Primary Examiner* — John S Kenyon
(74) *Attorney, Agent, or Firm* — Cooley LLP

(57) ABSTRACT

The present application relates to the use of roluperidone, i.e., Compound (I):

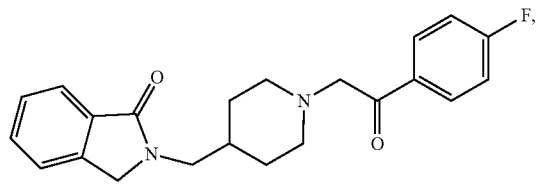

and salts, solvates, pharmaceutical compositions, and dosage forms thereof, for use in methods of treating negative symptoms and disorders (e.g., autism disorders, amblyopia, personality disorders, traumatic brain injury), as well as increasing neuroplasticity and promoting neuroprotection in subjects in need thereof.

20 Claims, 2 Drawing Sheets

(56) References Cited

OTHER PUBLICATIONS

Bi et al., "Childhood trauma interacted with BDNF Val66Met influence schizophrenic symptoms," Medicine, 2018, 97(13):e0160, 5 pages.

Bishara et al. "Upcoming Agents for the Treatment of Schizophrenia Mechanism of Action, Efficacy and Tolerability," Drugs, vol. 68, No. 16, p. 2269-2292, 2008.

Bonhaus D. et al., "[3H]BIMU-1, a 5-Hydroxytryptamine3 Receptor Ligand in NG-108 Cells, Selectively Labels Sigma-2 Binding Sites in Guinea Pig Hippocampus", The Journal of Pharmacology and Experimental Therapeutics, vol. 267, No. 2, p. 961-970, 1993.

Boone et al., "Relationship between positive and negative symptoms and neuropsychological scores in frontotemporal dementia and Alzheimer's disease," Journal of the International Neuropsychological Society (2003), 9, 698-709.

Buchanan et al. "Olanzapine Treatment of Residual Positive and Negative Symptoms", American Journal of Psychiatry, 2005, vol. 162, p. 124-129.

Buchanan et al. "Positive and Negative Symptom Response to Clozapine in Schizophrenic Patients With and Without the Deficit Syndrome", American Journal of Psychiatry, 1998, vol. 155, p. 751-760.

Buckley, P.F. et al. "Pharmacological treatment of negative symptoms of schizophrenia: therapeutic opportunity or Cul-de-sac?" Acta Psychiatrica Scandinavica, vol. 115, No. 2, 2007, p. 93-100.

Caira, "Crystalline Polymorphism of Organic Compounds," Topics in Current Chemistry, Springer, Berlin, De, vol. 198, Jan. 1, 1998, pp. 163-208.

Carlson, P. J. et al., "Neural circuitry and neuroplasticity in mood disorders: insights for novel therapeutic targets," NeuroRx 2006, 3(1): 22-41.

Caroni, P. et al., "Structural plasticity upon learning: regulation and functions," Nat Rev Neurosci 2012, 13(7): 478-90.

Casson et al., "Translational neuroprotection research in glaucoma: a review of definitions and principles," Clinical and Experimental Ophthalmology, 2012, 40(4): 350-357.

Chaudhury et al., "Neuropsychiatric Sequelae of Head Injury," Indian Journal of Neurotrauma (IJNT), 2005, vol. 2, No. 1, 13-21.

Cohrs, "Sleep Disturbances in Patients with Schizophrenia", CNS Drugs, (2008), vol. 22, No. 11, pp. 939-962.

Cramer, S. C. et al., "Harnessing neuroplasticity for clinical applications," Brain, 2011; 134 (Pt. 6): 1591-1609.

Davidson, M. et al., "MIN-101: A Drug in Development for the Treatment of Negative Symptoms in Schizophrenia", Poster presentation at the 55th Annual Meeting of the American College of Neuropsychopharmacology, held Dec. 4-8, 2016 in Hollywood, Florida, available on goo.gl/MIR7Tn.

Davidson, M. et al., "MIN-101: A sigma2 and 5HT2 antagonist drug in development for the treatment of symptomatically stable schizophrenia patients with negative symptoms", Oral Presentation at the 55th Annual Meeting of the American College of Neuropsychopharmacology, Dec. 4-8, 2016 in Hollywood, Florida, available on goo.Jl/xF5rdR.

Disner, S. G. et al., "Neural mechanisms of the cognitive model of depression," Nat Rev Neurosci 2011, 12(8): 467-477.

Dow, "Using Dow Excipients for Controlled Release of Drugs in Hydrophmc Matrix Systems," Dow, Sep. 2006, 36 pages.

Dumont M. et al. "Interaction of 1,3-di(2-[5-3H]tolyl) guanidine with σ2 binding sites in rat heart membrane preparations," European Journal of Pharmacology, 1991, vol. 209, p. 245-248.

Dutheil et al. "Xenobiotic metabolozing enzymes in the central nervous system: Contribution of cytochrome P450 enzymes in normal and pathological human brain," Biochimie, vol. 90, Issue 3, Mar. 2008, pp. 426-436.

Enciu, A. M. et al., "Neuroregeneration in neurodegenerative disorders," BMC Neurology 2011, 11:75, 7 pages.

Evonik Industries, "It's not Rocket Science to Reach Higher Coating Efficiency: PlasACRYL makes it possible," Evonik Industries AG, Oct. 2012, 8 pages.

Foussias, G. et al. "Negative Symptoms in Schizophrenia: Avolition and Occam's Razor," Schizophrenia Bulletin, 2010, vol. 36, No. 2, p. 359-369.

Galynker et al., "Negative Symptoms in Patients With Major Depressive Disorder: A Preliminary Report," Neuropsychiatry, Neuropsychology, and Behavioral Neurology, Jul. 2000, vol. 13, No. 3, 171-176.

Galynker et al., "Negative Symptoms in Stroke Patients and Length of Hospital Stay," The Journal of Nervous & Mental Disease, 1997, vol. 185(10), pp. 616-621.

Garza H. et al., "Characterization of a (+)-Azidophenazocine-Sensitive Sigma Receptor on Splenic Lymphocytes," The Journal of Immunology, 1993, vol. 151, p. 4672-4680.

Getz et al., "Negative Symptoms in Temporal Lobe Epilepsy," Am. J. Psychiatry, 2002; 159:644-651.

Geva, M. et al., "Pridopidine activates neuroprotective pathways impaired in Huntington's Disease," Human Molecular Genetics, 2016, vol. 25, No. 18, pp. 3975-3987.

Giacobbo et al., "Brain-Derived Neurotrophic Factor in Brain Disorders: Focus on Neuroinflammation," Molecular Neurobiology, 2019, vol. 56, Issue 5, pp. 3295-3312.

Gilmore, D. et al., "Review of the Pharmacological and Clinical Profile of Rimcazole", CNS Drug Reviews, 2004, vol. 10, No. 1, pp. 1-22.

Grande, I. et al., "The role of BDNF as a mediator of neuroplasticity in bipolar disorder," Psychiatry Investig. 2010; 7(4): 243-250.

Hashimoto et al., "Interactions of erythro-ifenprodil, threo-ifenprodil, erythro-iodoifenprodil, and eliprodil with subtypes of sigma- receptors" European Journal of Pharmacology, 273 (1995), pp. 307-310.

Hashimoto et al., "Sigma Receptor Ligands: Possible Application as Therapeutic Drugs and as Radiopharmaceuticals," Current Pharmaceutical Design, 2006, vol. 12, No. 30, pp. 3857-3876.

Herbener et al., "Longitudinal Assessment of Negative Symptoms in Schizophrenia/Schizoaffective Patients, Other Psychotic Patients, and Depressed Patients," Schizophrenia Bulletin, 2001, 27(3):527-537.

Hussan et al., "A review on recent advances of enteric coating," IOSR Journal of Pharmacy, vol. 2, Issue 6, 2012, 5-11.

Ishihara et al., Japanese Journal of Neuropsychopharmacology, (2002), vol. 22, No. 1, pp. 23-30 with partial English translation.

Jaen J. et al., "Evaluation of the Effects of the Enantiomers of Reduced Haloperidol, Azaperol, and Related 4-Amino-1-arylbutanols on Dopamine and a Receptors," J. Med. Chern., 1993, vol. 36, pp. 3929-3936.

Jeste, "Schizoaffective Disorder," National Alliance on Mental Illness, http://www.nami.org/Template.cfm?Section=By_Illness &Template=/ContentManagement!ContentDisplay.cfm&ContentiD= 23043 Wayback Internet Archive, (Nov. 7, 2008).

Jones C. et al., "Animal Models of Schizophrenia," British Journal of Pharmacology, 2011, vol. 164, pp. 1162-1194.

Kamel et al., "Pharmaceutical significance of cellulose: A review," eXPRESS Polymer Letters, (2008) vol. 2, No. 11, pp. 758-778.

Kay, "The Positive and Negative Syndrome Scale (PANSS) for Schizophrenia," Schizophrenia Bulletin, 1987, vol. 13, No. 2, pp. 261-276.

Kropp et al., "Cytochrome P-450 2D6 and 2C19 polymorphisms and length of hospitalization in psychiatry", Clinical Laboratory, 2006, 52(5-6), pp. 237-240. Abstract.

Latremoliere, A. and Woolf, C. J., "Central sensitization: a generator of pain hypersensitivity by central neural plasticity," J Pain 2009, 10(9): 895-926.

Luthringer, R., "Comparison of Three Sigma2 Ligands on Negative and Positive Symptoms of Schizophrenia", Exhibit C to Supplemental Declaration or Remy Luthringer Under 37 C.F.R. 1.132, Submitted Jan. 17, 2017 in U.S. Appl. No. 13/810,772, 14 pages.

Madsen, H. B. et al., "Neuroplasticity in addiction: cellular and transcriptional perspectives," Front. Mol. Neurosci. 2012, 5:99, 16 pages.

Malik, M. et al. "The Effects of Sigma (σ1) Receptor Selective Ligands on Muscarinic Receptor Antagonist Induced Cognitive Deficits in Mice" Br J of Pharmacology, (2015) 172(10):2519-2531.

(56) References Cited

OTHER PUBLICATIONS

Marder et al., "Aripiprazole in the treatment of schizophrenia: safety and tolerability in short-term, placebo-controlled trials," Schizophrenia Research, 2003, vol. 61, pp. 123-136.

Mash et al., "Sigma Receptors Are Associated With Cortical Limbic Areas in the Primate Brain," Synapse, 1992, vol. 12, pp. 195-205.

Maurice et al., "The attenuation of learning impairments induced after exposure to CO or trimethyltin in mice by sigma(sigma) receptor ligands involves both sigma 1 and sigma 2 sites," British Journal of Pharmacology, May 1999, 127(2), pp. 335-342.

McCArthy, K. D. and de Vellis, J., "Preparation of separate astroglialand oligodentroglialcell cultures from rat cerebral tissue," J Cell Biol, (1980) 85(3), 890-902.

Meltzer et al., "Lack of Involvement if Haloperidol-Sensitive Sigma Binding Sites in Modulation of Dopamine Activity and Induction of Dystonias by Antipsychotic Drugs," Neuropharmacology, 1992, vol. 31, No. 9, pp. 961-967.

Modell S. et al., "Efficacy and Safety of an Opiate Sigma-Receptor Antagonist (SL 82.0715) in Schizophrenic Patients with Negative Symptoms: and Open Dose-Tange Study," Pharmacopsychiat., 1996, vol. 29, pp. 63-66.

Nieto et al., "BDNF and schizophrenia: from neurodevelopment to neuronal plasticity, learning and memory," Frontiers in Psychiatry, Jun. 2013, 4:45, 11 pages.

Nokhodchi, et al., "The Role of Oral Controlled Release matrix Tablets in Drug Delivery Systems", BioImpacts, 2012, 2(4), pp. 175-187.

Paykel, Eugene S., "Basic Concepts of Depression", Dialogues in Clinical Neuroscience, 2008, vol. 10, No. 3, pp. 279-289.

Quirion et al., "A proposal for the classification of sigma binding sites", TiPS, Mar. 1992, vol. 13, pp. 85-86.

Reick et al., "Expression of brain-derived neurotrophic factor in astrocytes—Beneficial effects of glatiramer acetate in the R6/2 and YAC128 mouse models of Huntington's disease," Experimental Neurology, 2016, vol. 285, pp. 12-23.

Sahlholm, K. et al., "The dopamine stabilizers ACR16 and (-)-OSU6162 display nanomolar affinities at the σ-1 receptor," Mol. Psychiatry. (2013);18(1):12-14.

Schwarcz G. et al., "Open Label Evaluation of the Novel Antipsychotic Compound BW234U in Chronic Schizophrenics," Drug Development Research, 1985, vol. 5, pp. 387-393.

SEC Form 8-K filed Jun. 6, 2016, Minerva Neurosciences. Inc., 57 pages.

Seo, M.K. et al., "Effects of Antipsychotic Drugs on the Epigenetic Modification of Brain-Derived Neurotrophic Factor Gene Expression in the Hippocampi of Chronic Restraint Stress Rats," Neural Plasticity, 2018, vol. 2018, Article ID 2682037, 10 pages.

Sie, M., "An Update on Sleep Disorders and Their Treatment," Progress in Neurology and Psychiatry, 2010, 14(3): pp. 9-20.

Singhal, D et al., "Drug Polymorphism and Dosage Form Design: A practical perspective," Advanced Drug Delivery Reviews, 2004, 56, pp. 335-347.

Siris, Samuel G., "Depression in Schizophrenia: Perspective in the Era of 'Atypical' Antipsychotic Agents," Am. J. Psychiatry, Sep. 2000, vol. 157, No. 9, pp. 1379-1389.

Su, C. et al., "Progesterone increases the release of brain-derived neurotrophic factor from glia via progesterone receptor membrane component 1 (Pgrmc1)-dependent ERK5 signaling," Endocrinology (2012) 153(9):4389-4400.

Summary of 3rd Quarter Financial Results for year ended Mar. 31, 2010 (Unaudited); Mitsubishi Tanabe Pharma Corporation; Jan. 28, 2010, 25 pages, available on http://www.mt-pharma.co.jp/.

Takahashi et al. "Antipsychotic reverse abnormal EEG complexity in drug-naïve schizophrenia: A multiscale entropy analysis," NeuroImage, (2010), vol. 51, pp. 173-182.

Today's Therapy 2002, vol. 44, pp. 609-612.

Tokuda, "Pharmacological action of antipsychotic drugs," Folia Pharmacologica Japonica, (2006), vol. 128, pp. 173-176. (with English abstract).

Utami et al., "BDNF (brain-derived neurotrophic factor) serum levels in schizophrenic patients with cognitive deficits," IOP Conference Series: Earth and Environmental Science, 2018, vol. 125, 012181, 6 pages.

"View of NCT00861796 on Mar. 12, 2009", ClinicalTrials.gov archive, Mar. 12, 2009 Retrieved from the Internet: URL:http://clinicaltrials.gov/archive/NCT00861796/2009_03_12 6 pages.

Walker J. M. et al., "Sigma Receptors: Biology and Function," Pharmacological Reviews, 1990, vol. 42, No. 4, p. 355-402.

Werbeloff et al., "The Association between Negative Symptoms, Psychotic Experiences and Later Schizophrenia: A Population-Based Longitudinal Study," PLoS ONE (2015) 10(3): e0119852 12 pages.

White et al., "Empirical Assessment of the Factorial Structure of Clinical Symptoms in Schizophrenia," Psychopathology 1997:30:263-274.

Whittemore E. et al. "Antagonism of N-Methyl-D-Aspartate Receptors by s Site Ligands: Potency, Subtype-Selectivity and Mechanisms of Inhibition," The Journal of Pharmacology and Experimental Therapeutics, 1997, vol. 282, No. 1, p. 326-338.

Winograd-Gurvich et al., "Negative symptoms: A review of schizophrenia, melancholic depression and Parkinson's disease," Brain Research Bulletin 70 (2006) 312-331.

Yang et al. "Clinical significance of sleep EEG abnormalities in chronic schizophrenia", Schizophrenia Research, 2006, vol. 82, pp. 251-260.

Okuyama, S. Nippon Yakurigaku Zasshi, Folia Pharmacologica Japonica, 1999, vol. 114, pp. 12-23 (English abstract only).

Zhanpei, Zhen "Negative Symptoms of Schizophrenia", Foreign Medicine, Psychiatry Volume, Mar. 1988. (English translation of Chinese Office Action for Chinese Application No. 201180045067.1 attached).

Costa e Silva, "Sleep disorders in psychiatry," Metabolism Clinical and Experimental, 2006, 55, Supplement 2, S40-S44.

Keefe et al., "Cognitive Effects of MIN-101 in Patients With Schizophrenia and Negative Symptoms Results From a Randomized Controlled Trial," J Clin Psychiatry, May/Jun. 2018, 79:3, e1-e6.

Rusconi et al., "SSRI antidepressants and negative schizophrenic symptoms: differences between paroxetine and fluvoxamine in patients treated with olanzapine," Riv Psichiatr. Sep.-Oct. 2009;44(5):313-319 (English abstract only).

Zhou et al., "A new form of rapid binocular plasticity in adult with amblyopia," Scientific Reports, Sep. 2013, 3:2638, 5 pages.

* cited by examiner

USE OF ROLUPERIDONE TO TREAT NEGATIVE SYMPTOMS AND DISORDERS, INCREASE NEUROPLASTICITY, AND PROMOTE NEUROPROTECTION

RELATED APPLICATIONS

This application claims priority to, and the benefit of, U.S. Provisional Application No. 62/720,667, filed on Aug. 21, 2018, and U.S. Provisional Application No. 62/831,535 filed on Apr. 9, 2019, the contents of which are incorporated herein by reference in their entireties.

FIELD OF THE DISCLOSURE

This application relates to the use of roluperidone, i.e., Compound (I), and salts, solvates, pharmaceutical compositions, and dosage forms thereof, for use in methods of treating negative symptoms and disorders (e.g., autism disorders, amblyopia, personality disorders, traumatic brain injury), as well as increasing neuroplasticity and promoting neuroprotection in subjects in need thereof.

BACKGROUND OF THE DISCLOSURE

Brain-Derived Neurotrophic Factor (BDNF) is a member of a family of proteins called neurotrophins that play an important role in the formation and function of neural connections. BDNF is the most widely distributed neurotrophin in the brain and has been associated with neurogenesis, neuroplasticity, neuroprotection, synapse regulation, learning, and memory. (BDNF and schizophrenia: from neurodevelopment to neuronal plasticity, learning and memory, R. Nieto et al, Frontiers in Psychiatry, June 2013, Volume 4 Article 45.) Involvement in schizophrenia (Childhood trauma interacted with BDNF Val66Met influence schizophrenic symptoms, Xiao-Jiao Bi et al, Medicine. 97(13):e0160, Mar. 2018.) and other brain disorders has also been described. (Giacobbo et al. Molecular Neurobiology Volume 56, pages 3295-3312 (2019).)

An emerging body of evidence has pointed to a link between BDNF and disorders of the central nervous system. Epigenetic changes in the BDNF gene have been shown to be related to the pathophysiology of schizophrenia, and the reduced expression of BDNF has been identified in the frontal cortex and hippocampus of the brain in patients with schizophrenia. (Effects of Antipsychotic Drugs on the Epigenetic Modification of Brain-Derived Neurotrophic Factor Gene Expression in the Hippocampi of Chronic Restraint Stress Rats, M. K. Seo et al., Neural Plasticity, Volume 2018, Article ID 2682037, 10 pages.)

Researchers believe that lower than normal levels of BDNF may affect the pathogenesis of schizophrenia by contributing to altered brain development and abnormalities in neuroplasticity and synaptic function. These disturbances may explain certain morphological and neurochemical characteristics in the brains of patients with schizophrenia. (BDNF and schizophrenia: from neurodevelopment to neuronal plasticity, learning and memory, R. Nieto et al, Frontiers in Psychiatry, June 2013, Volume 4 Article 45.)

Furthermore, a functional polymorphism in the BDNF gene has been observed to interact with environmental factors in the development of psychoses including schizophrenia and bipolar disorders. (Xiao-Jiao Bi et al, Medicine. 97(13):e0160, March, 2018.) Additional studies have found an association between higher levels of BDNF and improved cognitive function in schizophrenic patients and improved neuropsychological function. It has been shown that BDNF protects astrocytes from cell death through TrkB-T1 signaling, exerts antioxidant action and induces release of neuroprotective factors from astrocytes. (BDNF (Brain-Derived Neurotrophic Factor) serum levels in schizophrenic patients with cognitive deficits, (N. Utami et al., "BDNF (brain-derived neurotrophic factor) serum levels in schizophrenic patients with cognitive deficits", doi:10.1088/1755-1315/125/1/012181.)

Thus, BDNF plays a crucial role in development and plasticity of the brain and is widely implicated in some psychiatric disorders. Epigenetic changes in the BDNF gene have been shown to be related to the pathophysiology of schizophrenia, and the reduced expression of BDNF has been identified in the frontal cortex and hippocampus of the brain in patients with schizophrenia.

Roluperidone hydrochloride, i.e., Compound (I), is being developed by Minerva Neurosciences, Inc. (Waltham, Mass.) for treating negative symptoms in schizophrenia patients. Compound (I) is a drug candidate with equipotent affinities for 5-hydroxytryptamine-2A (5-HT$_{2A}$) and sigma 2 and, at lower affinity levels, α1-adrenergic receptors. Compound (I) exhibits no affinity for dopaminergic, muscarinic, cholinergic and histaminergic receptors. Compound (I) has no direct dopaminergic post-synaptic blocking effects, known to be involved in some side effects like extrapyramidal symptoms, sedation, prolactin increases and weight gain.

SUMMARY OF THE DISCLOSURE

One aspect of this application pertains to a method of treating or diminishing at least one negative symptom in a subject, comprising administering a therapeutically effective amount of Compound (I),

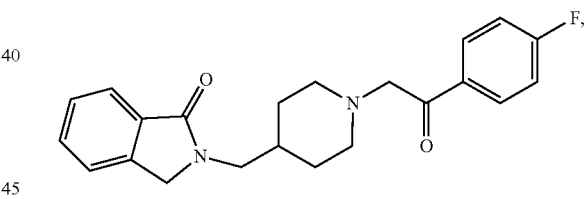

or a pharmaceutically acceptable salt or hydrate thereof, to the subject.

In one embodiment, the administration of Compound (I) starts before the manifestation of a first positive symptom in the subject.

In one embodiment, the administration of Compound (I) starts concurrently with the manifestation of a first positive symptom in the subject.

In one embodiment, the positive symptom is a hallucination, delusion, disorganized thinking, movement disorder, or depersonalization.

In one embodiment, the negative symptom is anhedonia, blunted affect, emotional withdrawal, poor rapport, passive/apathetic social withdrawal, difficultly in abstract thinking, lack of spontaneity or flow of conversation, or stereotyped thinking.

In one embodiment, the subject is schizophrenic.

In one embodiment, the subject is non-schizophrenic.

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to a method of treating or diminishing amblyopia in a subject in need thereof, comprising administering a therapeutically effective amount of Compound (I),

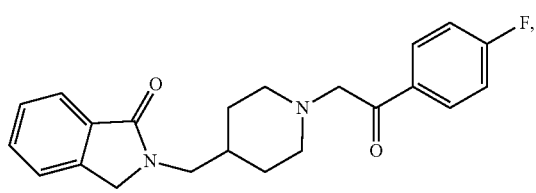 [SMILES: O=C(CN1CCC(CN2Cc3ccccc3C2=O)CC1)c1ccc(F)cc1]

or a pharmaceutically acceptable salt or hydrate thereof, to the subject.

One aspect of this application pertains to a method of treating an autism disorder in a subject in need thereof, comprising administering a therapeutically effective amount of Compound (I),

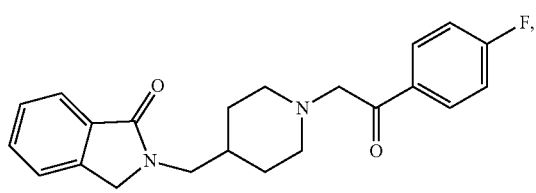 [SMILES: O=C(CN1CCC(CN2Cc3ccccc3C2=O)CC1)c1ccc(F)cc1]

or a pharmaceutically acceptable salt or hydrate thereof, to the subject.

In one embodiment, the autism disorder is classic autism, Asperger's syndrome, childhood disintegrative disorder, Rett syndrome, pervasive developmental disorders—not otherwise specified, fragile X syndrome, or a combination thereof.

A further aspect of this application that pertains to any of the methods disclosed herein, wherein the administration of Compound (I) increases neuroplasticity in the subject compared with a subject not administered Compound (I), or a pharmaceutically acceptable salt or hydrate thereof.

A further aspect of this application that pertains to any of the methods disclosed herein, wherein the administration of Compound (I) promotes neuroprotection or neural regeneration in the subject compared with a subject not administered Compound (I), or a pharmaceutically acceptable salt or hydrate thereof.

A further aspect of this application that pertains to any of the methods disclosed herein, wherein the therapeutically effective amount of Compound (I) is administered to the subject once or twice daily for 1 month, 2 months, 3 months, 4 months, 5 months, 6 months, or longer.

A further aspect of this application that pertains to any of the methods disclosed herein, wherein the subject is also administered an antipsychotic. In one embodiment, the antipsychotic is a typical antipsychotic selected from group consisting of haloperidol, loxapine, thioridazine, molindone, thiothixene, fluphenazine, mesoridazine, trifluoperazine, perphenazine, and chlorpromazine. In one embodiment, the antipsychotic is an atypical antipsychotic selected from group consisting of risperidone, olanzapine, clozapine, quetiapine, ziprasidone, aripiprazole, seritindole, zotepine, and perospirone.

A further aspect of this application that pertains to any of the methods disclosed herein, wherein the subject is less than 50, 40, 30, 25, 20, 19, 18, 17, 16, 15, 14, 13, 12, or 11 years old.

One aspect of this application pertains to a method of increasing neuroplasticity in a subject in need thereof, comprising administering an effective amount of Compound (I),

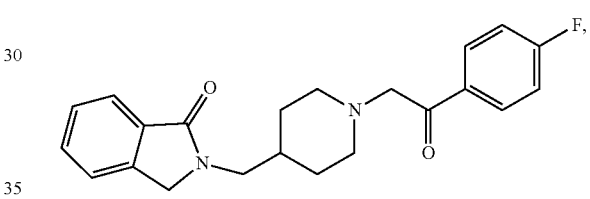

or a pharmaceutically acceptable salt or hydrate thereof, to the subject.

In one embodiment, the subject is schizophrenic.

In one embodiment, the subject is non-schizophrenic

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to a method of promoting neuroprotection in a subject in need thereof, the method comprising contacting a neuronal cell with an effective amount of Compound (I),

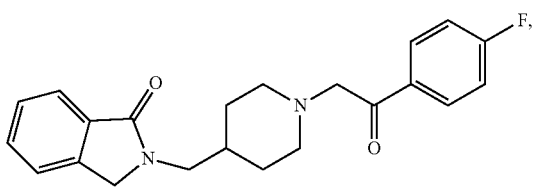 [SMILES: O=C(CN1CCC(CN2Cc3ccccc3C2=O)CC1)c1ccc(F)cc1]

or a pharmaceutically acceptable salt or hydrate thereof, wherein said contacting prevents or delays neuronal cell death relative to neuronal cell death occurring in the absence of said contacting, or wherein said contacting promotes nerve regeneration by stimulating neuronal growth.

In one embodiment, the subject is schizophrenic.

In one embodiment, the subject is non-schizophrenic.

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to a method of increasing brain-derived neurotropic factor (BDNF) expression in a cell, comprising contacting the cell with an effective amount of Compound (I),

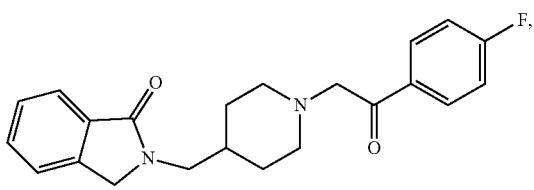 [SMILES: O=C(CN1CCC(CN2Cc3ccccc3C2=O)CC1)c1ccc(F)cc1]

or a pharmaceutically acceptable salt or hydrate thereof.

In one embodiment, the contacting is in vitro.

In one embodiment, the contacting is in vivo.

One aspect of this application pertains to a method of increasing glial cell line-derived neurotrophic factor (GDNF) expression in a cell, comprising contacting the cell with an effective amount of Compound (I),

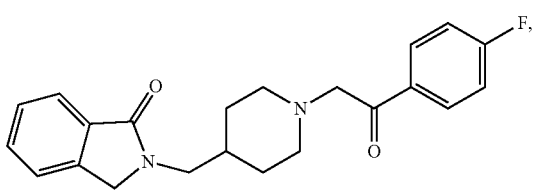 [SMILES: O=C(CN1CCC(CN2Cc3ccccc3C2=O)CC1)c1ccc(F)cc1]

or a pharmaceutically acceptable salt or hydrate thereof.

In one embodiment, the contacting is in vitro.

In one embodiment, the contacting is in vivo.

One aspect of this application pertains to a method of treating or diminishing a disorder in a subject in need thereof, comprising administering a therapeutically effective amount of Compound (I),

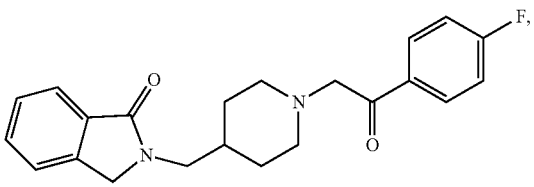 [SMILES: O=C(CN1CCC(CN2Cc3ccccc3C2=O)CC1)c1ccc(F)cc1]

or a pharmaceutically acceptable salt or hydrate thereof, to the subject, wherein the disorder is selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, and Tourette's syndrome.

One aspect of this application pertains to a therapeutically effective amount of Compound (I),

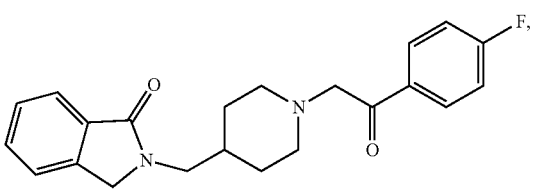 [SMILES: O=C(CN1CCC(CN2Cc3ccccc3C2=O)CC1)c1ccc(F)cc1]

or a pharmaceutically acceptable salt or hydrate thereof, for use in the treatment or diminishing of at least one negative symptom in a subject.

In one embodiment, the use of Compound (I) starts before the manifestation of a first positive symptom in the subject.

In one embodiment, the use of Compound (I) starts concurrently with the manifestation of a first positive symptom in the subject.

In one embodiment, the positive symptom is a hallucination, delusion, disorganized thinking, movement disorder, or depersonalization.

In one embodiment, the negative symptom is anhedonia, blunted affect, emotional withdrawal, poor rapport, passive/apathetic social withdrawal, difficultly in abstract thinking, lack of spontaneity or flow of conversation, or stereotyped thinking.

In one embodiment, the subject is schizophrenic.

In one embodiment, the subject is non-schizophrenic.

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to a therapeutically effective amount of Compound (I),

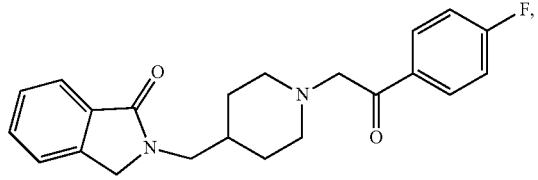 [SMILES: O=C(CN1CCC(CN2Cc3ccccc3C2=O)CC1)c1ccc(F)cc1]

or a pharmaceutically acceptable salt or hydrate thereof, for use in the treatment or diminishing of amblyopia in a subject suffering from amblyopia.

One aspect of this application pertains to a therapeutically effective amount of Compound (I),

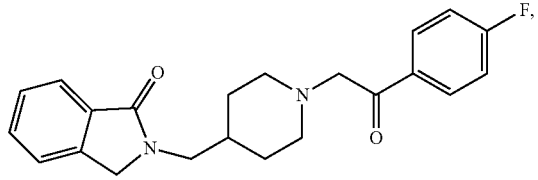 [SMILES: O=C(CN1CCC(CN2Cc3ccccc3C2=O)CC1)c1ccc(F)cc1]

or a pharmaceutically acceptable salt or hydrate thereof, for use in the treatment of an autism disorder in a subject suffering from an autism disorder. In one embodiment, the autism disorder is classic autism, Asperger's syndrome, childhood disintegrative disorder, Rett syndrome, pervasive developmental disorders—not otherwise specified, fragile X syndrome, or a combination thereof.

A further aspect of this application that pertains to any of the uses disclosed herein, wherein the use of Compound (I) increases neuroplasticity in the subject compared with a subject where Compound (I) is not used.

A further aspect of this application that pertains to any of the uses disclosed herein, wherein the use of Compound (I) promotes neuroprotection or neural regeneration in the subject compared with a subject where Compound (I) is not used.

A further aspect of this application that pertains to any of the uses disclosed herein, wherein the therapeutically effective amount of Compound (I) is administered to the subject once or twice daily for 1 month, 2 months, 3 months, 4 months, 5 months, 6 months, or longer.

A further aspect of this application that pertains to any of the uses disclosed herein, wherein the subject is also administered an antipsychotic. In one embodiment, the antipsychotic is a typical antipsychotic selected from group consisting of haloperidol, loxapine, thioridazine, molindone, thiothixene, fluphenazine, mesoridazine, trifluoperazine, perphenazine, and chlorpromazine. In one embodiment, the antipsychotic is an atypical antipsychotic selected from group consisting of risperidone, olanzapine, clozapine, quetiapine, ziprasidone, aripiprazole, seritindole, zotepine, and perospirone.

A further aspect of this application that pertains to any of the uses disclosed herein, wherein the subject is less than 50, 40, 30, 25, 20, 19, 18, 17, 16, 15, 14, 13, 12, or 11 years old.

One aspect of this application pertains to an effective amount of Compound (I),

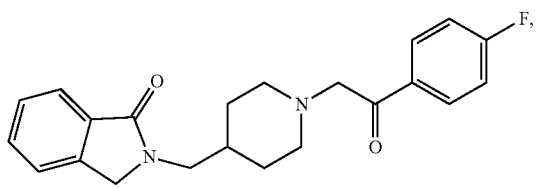 [SMILES: O=C(CN1CCC(CN2Cc3ccccc3C2=O)CC1)c1ccc(F)cc1]

or a pharmaceutically acceptable salt or hydrate thereof, for use in increasing neuroplasticity in a subject in need thereof.

In one embodiment, the subject is schizophrenic.

In one embodiment, the subject is non-schizophrenic

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to an effective amount of Compound (I),

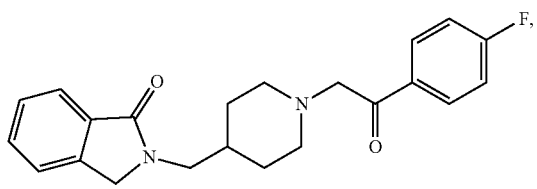 [SMILES: O=C(CN1CCC(CN2Cc3ccccc3C2=O)CC1)c1ccc(F)cc1]

or a pharmaceutically acceptable salt or hydrate thereof, for use in promoting neuroprotection in an subject in need thereof, comprising contacting a neuronal cell with the effective amount of Compound (I) and wherein said contacting prevents or delays neuronal cell death relative to neuronal cell death occurring in the absence of said contacting, or wherein said contacting promotes nerve regeneration by stimulating neuronal growth.

In one embodiment, the subject is schizophrenic.

In one embodiment, the subject is non-schizophrenic.

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to an effective amount of Compound (I),

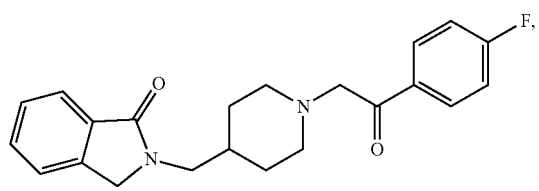 [SMILES: O=C(CN1CCC(CN2Cc3ccccc3C2=O)CC1)c1ccc(F)cc1]

or a pharmaceutically acceptable salt or hydrate thereof, for use in increasing brain-derived neurotropic factor (BDNF) expression in a cell, comprising contacting the cell with the effective amount of Compound (I).

In one embodiment, the contacting is in vitro.

In one embodiment, the contacting is in vivo.

One aspect of this application pertains to an effective amount of Compound (I),

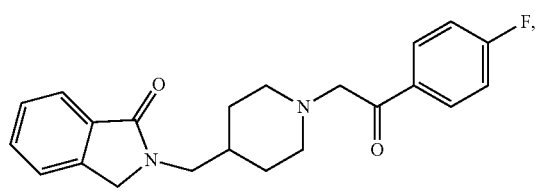 [SMILES: O=C(CN1CCC(CN2Cc3ccccc3C2=O)CC1)c1ccc(F)cc1]

or a pharmaceutically acceptable salt or hydrate thereof, for use in increasing glial cell line-derived neurotropic factor (GDNF) expression in a cell, comprising contacting the cell with the effective amount of Compound (I).

In one embodiment, the contacting is in vitro.

In one embodiment, the contacting is in vivo.

One aspect of this application pertains to a therapeutically effective amount of Compound (I),

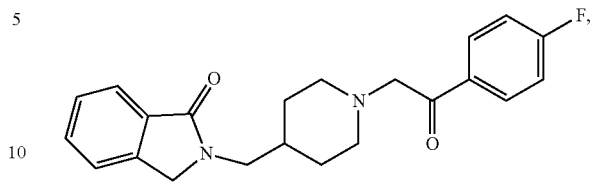

or a pharmaceutically acceptable salt or hydrate thereof, for use in the treatment or diminishing of a disorder in a subject in need thereof, wherein the disorder is selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, and Tourette's syndrome.

One aspect of this application pertains to a therapeutically effective amount of Compound (I),

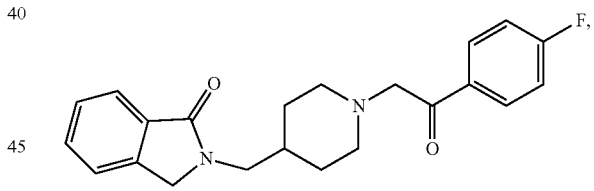

or a pharmaceutically acceptable salt or hydrate thereof, for use in the manufacture of a medicament for the treatment or diminishing of at least one negative symptom in a subject.

In one embodiment, the use of the medicament starts before the manifestation of a first positive symptom in the subject.

In one embodiment, the use of the medicament starts concurrently with the manifestation of a first positive symptom in the subject.

In one embodiment, the positive symptom is a hallucination, delusion, disorganized thinking, movement disorder, or depersonalization.

In one embodiment, the negative symptom is anhedonia, blunted affect, emotional withdrawal, poor rapport, passive/apathetic social withdrawal, difficultly in abstract thinking, lack of spontaneity or flow of conversation, or stereotyped thinking.

In one embodiment, the subject is schizophrenic.

In one embodiment, the subject is non-schizophrenic.

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to a therapeutically effective amount of Compound (I),

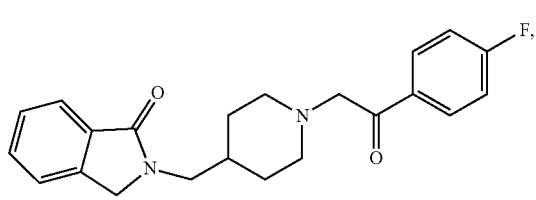 [SMILES: O=C(CN1CCC(CN2Cc3ccccc3C2=O)CC1)c1ccc(F)cc1]

or a pharmaceutically acceptable salt or hydrate thereof, for use in the manufacture of a medicament for the treatment or diminishing of amblyopia in a subject suffering from amblyopia.

One aspect of this application pertains to a therapeutically effective amount of Compound (I),

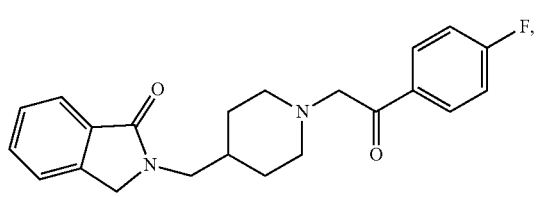 [SMILES: O=C(CN1CCC(CN2Cc3ccccc3C2=O)CC1)c1ccc(F)cc1]

or a pharmaceutically acceptable salt or hydrate thereof, for use in the manufacture of a medicament for the treatment of an autism disorder in a subject suffering from an autism disorder. In one embodiment, the autism disorder is classic autism, Asperger's syndrome, childhood disintegrative disorder, Rett syndrome, pervasive developmental disorders—not otherwise specified, fragile X syndrome, or a combination thereof.

A further aspect of this application that pertains to any of the uses disclosed herein, wherein the use of the medicament increases neuroplasticity in the subject compared with a subject where the medicament is not used.

A further aspect of this application that pertains to any of the uses disclosed herein, wherein the use of the medicament promotes neuroprotection or neural regeneration in the subject compared with a subject where the medicament is not used.

A further aspect of this application that pertains to any of the uses disclosed herein, wherein the medicament is administered to the subject once or twice daily for 1 month, 2 months, 3 months, 4 months, 5 months, 6 months, or longer.

A further aspect of this application that pertains to any of the uses disclosed herein, wherein the subject is also administered an antipsychotic. In one embodiment, the antipsychotic is a typical antipsychotic selected from group consisting of haloperidol, loxapine, thioridazine, molindone, thiothixene, fluphenazine, mesoridazine, trifluoperazine, perphenazine, and chlorpromazine. In one embodiment, the antipsychotic is an atypical antipsychotic selected from group consisting of risperidone, olanzapine, clozapine, quetiapine, ziprasidone, aripiprazole, seritindole, zotepine, and perospirone.

A further aspect of this application that pertains to any of the uses disclosed herein, wherein the subject is less than 50, 40, 30, 25, 20, 19, 18, 17, 16, 15, 14, 13, 12, or 11 years old.

One aspect of this application pertains to an effective amount of Compound (I),

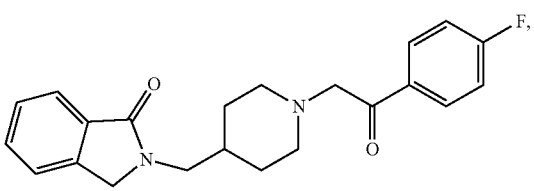 [SMILES: O=C(CN1CCC(CN2Cc3ccccc3C2=O)CC1)c1ccc(F)cc1]

or a pharmaceutically acceptable salt or hydrate thereof, for use in the manufacture of a medicament for increasing neuroplasticity in a subject in need thereof.

In one embodiment, the subject is schizophrenic.

In one embodiment, the subject is non-schizophrenic

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to an effective amount of Compound (I),

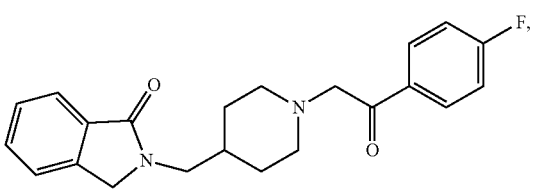 [SMILES: O=C(CN1CCC(CN2Cc3ccccc3C2=O)CC1)c1ccc(F)cc1]

or a pharmaceutically acceptable salt or hydrate thereof, for use in the manufacture of a medicament for promoting neuroprotection in an subject in need thereof, comprising contacting a neuronal cell with the effective amount of the medicament and wherein said contacting prevents or delays neuronal cell death relative to neuronal cell death occurring in the absence of said contacting, or wherein said contacting promotes nerve regeneration by stimulating neuronal growth.

In one embodiment, the subject is schizophrenic.

In one embodiment, the subject is non-schizophrenic.

In one embodiment, the subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application pertains to Compound (I),

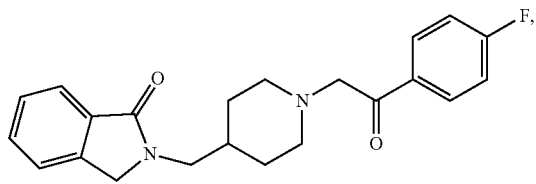 [SMILES: O=C(CN1CCC(CN2Cc3ccccc3C2=O)CC1)c1ccc(F)cc1]

or a pharmaceutically acceptable salt or hydrate thereof, for use in the manufacture of a medicament for increasing brain-derived neurotropic factor (BDNF) expression in a cell, comprising contacting the cell with an effective amount of the medicament.

In one embodiment, the contacting is in vitro.

In one embodiment, the contacting is in vivo.

One aspect of this application pertains to Compound (I),

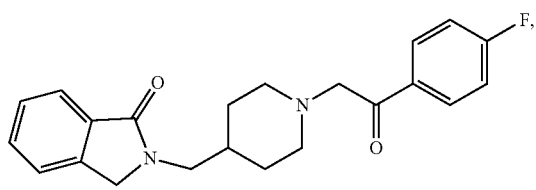 [SMILES: O=C(CN1CCC(CN2Cc3ccccc3C2=O)CC1)c1ccc(F)cc1]

or a pharmaceutically acceptable salt or hydrate thereof, for use in the manufacture of a medicament for increasing glial cell line-derived neurotropic factor (GDNF) expression in a cell, comprising contacting the cell with an effective amount of the medicament.

In one embodiment, the contacting is in vitro.

In one embodiment, the contacting is in vivo.

One aspect of this application pertains to a therapeutically effective amount of Compound (I),

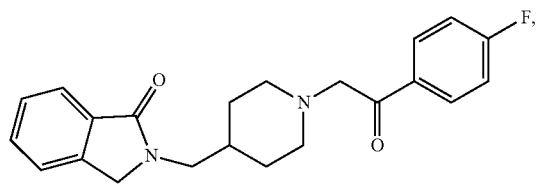 [SMILES: O=C(CN1CCC(CN2Cc3ccccc3C2=O)CC1)c1ccc(F)cc1]

or a pharmaceutically acceptable salt or hydrate thereof, for use in the manufacture of a medicament for the treatment or diminishing of a disorder in a subject in need thereof, wherein the disorder is selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, and Tourette's syndrome.

DETAILED DESCRIPTION

Figure 2:
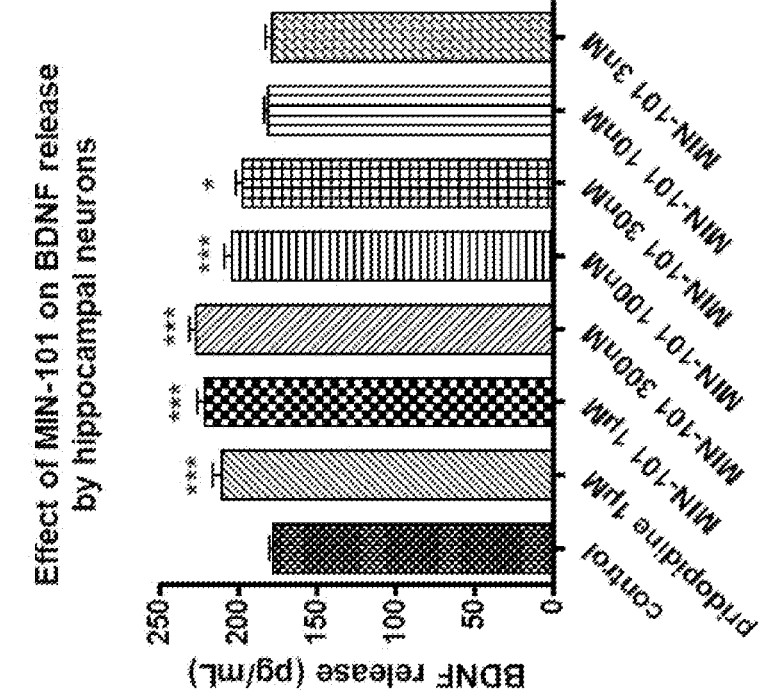
FIG. 2: Effect of Compound (I) on BDNF release by primary hippocampal neurons measured by in situ ELISA. Data are expressed in pg/mL (mean±sem; *$p<0.05$; $p<0.01$; *$p<0.001$; one way ANOVA followed by Dunnett's test).

BDNF, which is the most widely distributed member of neurotrophins in the brain, has been associated with neurogenesis, neuroplasticity, neuroprotection, synaptic regulation, learning, and memory. Dysregulation of BDNF has been described in the pathophysiology of schizophrenia and several other neuro-psychiatric disorders. The Results from a Phase 2b clinical study has shown a statistically significant benefit of both tested doses (32 mg and 64 mg) of Compound (I) over placebo in improving negative symptoms in schizophrenia. Our present results show that Compound (I) increased BDNF release by astrocytes and hippocampal neurons and GDNF release by astrocytes. Moreover Compound (I) is able to enhance the expression of BDNF at drug concentrations similar to those observed in human at tested doses. Therefore, in addition to the known neurotransmitter pathways targeted by Compound (I), particularly on the serotoninergic 5-HT2A and the sigma2 pathways, the effect of Compound (I) on BDNF and GDNF suggests that this compound may have the potential for disease modification, neuroprotection, improved neuroplasticity, and the treatment of negative symptoms in schizophrenic and non-schizophrenic subjects, as well as in the treatment of other diseases and disorders.

Understanding the mode of action of Compound (I) could potentially elucidate the neurobiology behind its clinical benefits. Its molecular binding profile shows strong affinity for $5-HT_{2A}$ receptors ($K_i$ 7.5 nmol/L) and $sigma_2$ receptors ($K_i$ 8.2 nmol/L), with a 30-fold selectivity versus $sigma_1$ receptors ($K_i$ 254 nmol/L). In addition, there is a significant affinity for alpha1-adrenergic receptors ($K_i$ 14.4 nmol/L). A leading hypothesis suggests that hypofunction in certain neurocircuits may contribute to a lack of synaptic plasticity underlying the pathogenesis of schizophrenia and notably negative symptoms.

Therefore, in addition to the known neurotransmitter pathways targeted by Compound (I), particularly the serotoninergic $5HT_{2A}$ and the sigma-2 pathways, Compound (I)'s effect on BDNF and GDNF suggests that this compound may have the potential for disease modification and improved neuroplasticity.

Modulating sigma receptors, for which the two known subtypes are sigma 1 (Sig1R) and sigma 2 (Sig2R), has only recently been explored as a possible strategy for treating central nervous system (CNS) disorders. (Sahlholm, K. et al. "The dopamine stabilizers ACR16 and (−)-OSU6162 display nanomolar affinities at the σ-1 receptor." Mol. Psychiatry. (2013); 18(1):12-4.) Both sigma receptor subtypes are expressed in the CNS and distinguished from one another based on their affinity for different ligands and biological profiles. The Sig2R, which was recently cloned (Alon, A. et al, "Identification of the gene that codes for the sigma 2 receptor" Proc. Natl. Acad. Sci. U.S.A. July 3; 114(27): 7160-7165, 2017) and identified as transmembrane protein 97 (TMEM97), is involved in cell proliferation, regulation of cytosolic calcium, cholesterol trafficking and homeostasis. Sig2R has long been associated with cancer and it is increasingly being implicated in cellular processes relevant to a variety of CNS disorders including Alzheimer's disease, schizophrenia, anxiety, pain and Niemann-Pick disease.

Compound (I), also referred to as roluperidone, roluperidone hydrochloride, MIN-101, and previously known as CYR-101 and MT-210, is being developed by Minerva Neurosciences, Inc. (Waltham, Mass.) for treating negative symptoms in schizophrenia patients (See U.S. Pat. No. 9,732,059, which is incorporated by reference in its entirety). Compound (I), has the chemical name 1H-Isoindol-1-one, 2-[[1-[2-(4-Fluorophenyl)-2-oxoethyl]-4-piperidinyl]methyl]-2,3-dihydro-, hydrochloride, hydrate (1:1: 2). The structure of the free base is:

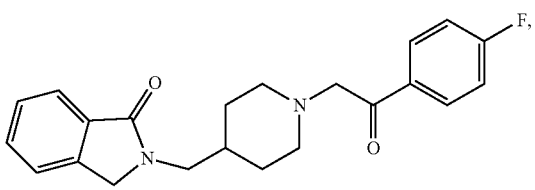 [SMILES: O=C(CN1CCC(CN2Cc3ccccc3C2=O)CC1)c1ccc(F)cc1]

As disclosed in U.S. Pat. Nos. 9,458,130, 9,730,920, and 10,258,614, the contents of which are incorporated herein in their entirety, QT prolongation in patients treated with Compound (I) has been observed and appears to be related to plasma levels of Compound (I) and more specifically to a metabolite identified as BFB-520. These patents disclose that QT prolongation induced by administration of Compound (I) can be reduced by administering this agent in a modified release (MR) formulation that provides a maximum plasma concentration ($C_{max}$) of Compound (I) and BFB-520 below 80 ng/mL and 12 ng/mL, respectively.

US 2016/0354357 discloses methods of treating sigma-2 receptor mediated disorders comprising administering Compound (I).

All references to Compound (I) herein include all pharmaceutically acceptable salts and/or all solvates (e.g., the hydrochloride dihydrate) and alternative physical forms thereof unless otherwise indicated. All doses recited herein are based on the molecular weight of the free base of Compound (I), which is 366.43 g/mole, rather than the molecular weight of the pharmaceutically acceptable salt or solvate (e.g., the hydrochloride dihydrate) thereof or any excipients in the composition, unless otherwise indicated.

All amounts of a component of an oral dosage form described herein that are indicated based on % w/w refer to the total weight of the oral dosage form, unless otherwise indicated.

The term "about" as part of a quantitative expression such as "about X", includes any value that is 10% higher or lower than X, and also includes any numerical value that falls between X-10% and X+10%. Thus, for example, a weight of about 40 g includes a weight of between 36 to 44 g.

"Administration" refers to introducing an agent, such as a Compound (I), or dosage form thereof, into a subject. The related terms "administering" and "administration of" (and grammatical equivalents) refer both to direct administration, which may be administration to a subject by a medical professional or by self-administration by the subject, and/or to indirect administration, which may be the act of prescribing a drug such as a dosage form described herein. For example, a physician who instructs a patient to self-administer a drug and/or provides a patient with a prescription for a drug is administering the drug to the patient.

"BNSS" is the Brief Negative Symptom Scale.

"Comprising" or "comprises" as applied to a particular dosage form, composition, use, method or process described or claimed herein means that the dosage form, composition, use, method, or process includes all of the recited elements in a specific description or claim, but does not exclude other elements. "Consists essentially of" and "consisting essentially of" means that the described or claimed composition, dosage form, method, use, or process does not exclude other materials or steps that do not materially affect the recited physical, pharmacological, pharmacokinetic properties or therapeutic effects of the composition, dosage form, method, use, or process. "Consists of" and "consisting of" means the exclusion of more than trace elements of other ingredients and substantial method or process steps.

"Controlled release" or "CR" as used herein with respect to an oral dosage form of the disclosure means that Compound (I) is released from the dosage form according to a pre-determined profile that may include when and where release occurs after oral administration and/or a specified rate of release over a specified time period.

"Controlled release agent" as used herein with respect to an oral dosage form of the disclosure refers to one or more substances or materials that modulate release of Compound (I) from the dosage form. Controlled release agents may be materials which are organic or inorganic, naturally occurring or synthetic, such as polymeric materials, triglycerides, derivatives of triglycerides, fatty acids and salts of fatty acids, talc, boric acid and colloidal silica.

"CYP2D6 allele" refers to one of over 100 named versions of the CYP2D6 gene that are present in the general population, and typically classified into one of three categories: active (functional); decreased activity (partially active or decreased function) and inactive (non-functional).

Active CYP2D6 alleles include: *1, *2, *2A, *33, *35, *39, *48, and *53.

Decreased activity CYP2D6 alleles include: *9, *10, *17, *29, *41, *49, *50, *54, *55, *59, *69, and *72.

Inactive CYP2D6 alleles include: *3, *4, *5 (deletion), *6, *7, *8, *11, *12, *13, *14A, *14B, *15, *18, *19, *20, *21, *38, *40, *42, *44, *56, *56A, *56B, and *68.

"CYP2D6 Extensive Metabolizer (EM) genotype" as applied to a subject means the subject has a CYP2D6 which results in CYP2D6 metabolic activity considered as normal. CYP2D6 EM genotypes include combinations of: (a) two active CYP2D6 alleles, (b) one active and one decreased activity CYP2D6 allele, and (c) one active and one inactive CYP2D6 allele.

"CYP2D6 Intermediate Metabolizer (IM) genotype" as applied to a subject means the subject has a CYP2D6 genotype, which results in reduced CYP2D6 metabolic activity. CYP2D6 IM genotypes include combinations of: (a) one inactive and one decreased activity CYP2D6 allele; and (c) two decreased activity CYP2D6 alleles.

"CYP2D6 PM genotype" as applied to a subject means the subject has a positive test result for a CYP2D6 poor metabolizer genotype and thus likely to have no CYP2D6 activity. A CYP2D6 PM genotype is 2 inactive alleles.

"CYP2D6 UM genotype" as applied to a subject means the subject has a positive test result for a CYP2D6 ultrarapid metabolizer genotype and thus likely to have higher than average CYP2D6 activity. A CYP2D6 UM genotype is 3 or more active alleles.

"Enteric coating" as used herein with respect to a dosage form of the disclosure refers to a pH-dependent material that surrounds a core comprising Compound (I) and which remains substantially intact in the acid environment of the stomach, but which dissolves in the pH environment of the intestines.

In one embodiment, in the dosage forms of the disclosure, the filler is selected from the group consisting of microcrystalline cellulose, lactose monohydrate, sucrose, glucose, and sorbitol.

"Glidant" as used herein refers to a substance used to promote powder flow by reducing interparticle cohesion. In one embodiment, in the dosage forms of the disclosure, the glidant is selected from the group consisting of silica colloidal anhydrous, starch, and talc.

"Lubricant" as used herein refers to a substance that prevents ingredients from sticking and/or clumping together in the machines used in preparation of the dosage forms of the disclosure. In one embodiment, in the dosage forms of the disclosure, the lubricant is selected from the group consisting of magnesium stearate, steric acid, and vegetable stearin.

"Fasted condition" or "fasted state" as used to describe a subject means the subject has not eaten for at least 4 hours before a time point of interest, such as the time of administering Compound (I) or a dosage form thereof. In an embodiment, a subject in the fasted state has not eaten for at least any of 6, 8, 10 or 12 hours prior to administration of Compound (I) or a dosage form thereof.

"Fed condition" or "fed state" as used to describe a subject herein means the subject has eaten less than 4 hours before a time point of interest, such as the time of administering Compound (I) or a dosage form thereof. In an embodiment, a subject in the fed state has not eaten for at least any of 3, 2, 1 or 0.5 hours prior to administration of Compound (I) or a dosage form thereof.

"Gastro-resistant" or "GR" as applied to a CR oral dosage form described herein means that release of Compound (I) in the stomach of a subject shall not exceed 5%, 2.5%, 1% or 0.5% of the total amount of Compound (I) in the dosage form.

"MIN-101" is a code name for Compound (I) or roluperidone hydrochloride, i.e., 1H-Isoindol-1-one, 2-[[1-[2-(4-Fluorophenyl)-2-oxoethyl]-4-piperidinyl]methyl]-2,3-dihydro-, hydrochloride, hydrate (1:1:2), with an alternative name of 2-{1-[2-(4-Fluorophenyl)-2-oxoethyl]piperidin-4-ylmethyl}-2,3-dihydroisoindol-1-one hydrochloride dihydrate.

"Oral dosage form" as used herein refers to a pharmaceutical drug product that contains a specified amount (dose) of Compound (I) as the active ingredient, or a pharmaceutically acceptable salt and/or solvate thereof, and inactive components (excipients), formulated into a particular configuration that is suitable for oral administration, such as a tablet or capsule. In one embodiment, the compositions are in the form of a tablet that can be scored.

"Pharmaceutically acceptable salt" as used herein with respect to Compound (I), means a salt form of Compound (I) as well as hydrates of the salt form with one or more water molecules present. Such salt and hydrated forms retain the biological activity of Compound (I) and are not biologically or otherwise undesirable, i.e., exhibit minimal, if any, toxicological effects. In an embodiment, the pharmaceutically acceptable salt of Compound (I) has a single HCl molecule and two water molecules, i.e., 1H-Isoindol-1-one, 2-[[1-[2-(4-Fluorophenyl)-2-oxoethyl]-4-piperidinyl]methyl]-2,3-dihydro-, hydrochloride, hydrate (1:1:2).

"PANSS" is Positive and Negative Syndrome Scale.

"Pharmacokinetic parameter" means a measurement or characteristic that describes the pharmacokinetic properties of a compound of interest. PK parameters used herein are defined below.

"AUC" is total area under the plasma concentration-time curve, which is a measure of exposure to a compound of interest, and is the integral of the concentration-time curve after a single dose or at steady state. AUC is expressed in units of ng·H/mL (ng×H/mL).

"$AUC_{(0-4H)}$" means the AUC from 0 hours to 4 hours after administration of a single dose.

"$AUC_{(0-24H)}$" means the AUC from 0 hours to 24 hours after administration of a single dose.

"$AUC_{last}$" means the AUC from time 0 to the last quantifiable concentration ($C_{last}$).

"$AUC_{(0-tau)}$" means the AUC from 0 hours to the end of a dosing interval.

"$C_{max}$" means the observed maximum (peak) plasma concentration of a specified compound, such as Compound (I), after administration of a dose of a composition comprising the compound. In an embodiment, the $C_{max}$ is measured after 2 or more doses of the composition. In an embodiment, the $C_{max}$ is measured when the specified compound reaches steady-state.

"$C_{min}$" means the observed minimum plasma concentration of a specified compound, such as Compound (I), after administration of a dose of a composition comprising the compound. In an embodiment, the $C_{max}$ is measured after 2 or more doses of the composition. In an embodiment, the $C_{max}$ is measured when the specified compound reaches steady-state.

"$C_{ss}$" means the concentration at the steady state.

"$C_{ave}$" means the average concentration which is the AUC over time ratio.

"$C_p$" means the plasma concentration of a specified compound, such as Compound (I), at any time T after administration of a dose of a composition comprising the compound.

"$C_{p(last)}$" means the last measured $C_p$, with reference to the time of collection of the last of a series of blood samples for assay for the specified compound.

"$C_{p(T)}$" means the $C_p$ at the specified time; thus $C_{p(4H)}$ and $C_{p(12H)}$ are the $C_p$ at 4 hours and 24 hours, respectively.

"H" means hours.

"PK" is pharmacokinetic(s).

"Steady-state" means the rate of absorption of a specified compound of interest such as Compound (I) is equal to the rate of elimination of the compound.

A "schizophrenic" subject refers to a subject that has been diagnosed with or suffers from schizophrenia. In one embodiment, the schizophrenic subject also suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

A "non-schizophrenic" subject refers to a subject that has not been diagnosed with and/or does not suffer from schizophrenia. In one embodiment, the non-schizophrenic subject still suffers from negative symptoms. In one embodiment, the non-schizophrenic subject has not been diagnosed with a psychiatric disorder. In one embodiment, the non-schizophrenic subject suffers from a disorder selected from the group consisting of amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

"Tau" means a dosing interval (H). For example, for once daily dosing, tau is 24 H, $T_{max}$ means the time to maximum (or peak) plasma or serum concentration of a specified therapeutic compound after administration of a single dose of a composition comprising the compound and before administration of a second dose.

$V_{max}$ means the maximum absorption rate (mg/H).

"Therapeutically effective amount", as used herein with respect to therapeutic uses of a dosage form comprising Compound (I) or pharmaceutically salt and/or solvate thereof, means an amount of the free base (Compound (I)) that is sufficient to treat, ameliorate, or prevent a specified disease, disease symptom (e.g., a negative symptom), disorder or condition, or to exhibit a detectable therapeutic or inhibitory effect. The effect can be detected by any assay method known in the art. The effective amount for a particular subject may depend upon the subject's body weight, size, and health; the nature and extent of the condition; and whether additional therapeutics are to be administered to the subject. Therapeutically effective amounts for a given situation can be determined by routine experimentation that is within the skill and judgment of the clinician.

An "effective amount" when used in connection with Compound (I), or a salt, hydrate, or pharmaceutical composition thereof, refers to an amount effective for promoting improved neuroplasticity or neuroprotection.

"Treat", "treating", "treatment" and similar terms, as used herein with respect to one or more specified disease symptoms shall include the management and care of a patient for the purpose of improving one or more of the specified symptoms, and include administration of compound (I), a composition thereof, or a dosage form thereof, at a dosing frequency and for a treatment period that are sufficient to prevent the onset of one or more of the symptoms, reduce the frequency, intensity or severity of one or more of the symptoms, delay or avoid the development of additional symptoms, or any combination of these treatment objectives. In an embodiment, the effect of treatment with compound (I), a composition thereof, or a dosage form thereof, is assessed by comparing the severity of the subject's symptoms at baseline (e.g., prior to treatment) and after at least one treatment period. In an embodiment, the treatment period is at least one week, at least two weeks, at least four weeks, at least six weeks, at least eight weeks, at least 10 weeks or at least twelve weeks or more. In an embodiment, the symptoms to be treated is at least one negative symptom in a schizophrenic or non-schizophrenic patient, the dosage form comprises 32 mg of Compound (I), the dosing frequency is once daily, and the treatment period is at least eight weeks.

Compound (I) may be synthesized using standard synthetic methods and procedures for the preparation of organic molecules and functional group transformations and manipulations, including the use of protective groups, as can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$; John Wiley & Sons: New York, 1999. A method for preparing Compound (I) is described in U.S. Pat. No. 7,166,617, the contents of which are incorporated herein in their entirety.

In an embodiment, the drug substance form of Compound (I) used in any of the methods herein is a dihydrate of a hydrochloride salt of Compound (I), which has the chemical name 1H-Isoindol-1-one, 2-[[1-[2-(4-Fluorophenyl)-2-oxoethyl]-4-piperidinyl]methyl]-2,3-dihydro-, hydrochloride, hydrate (1:1:2), which has a molecular formula of $C_{22}H_{23}FN_2O_2$, HCl, $2H_2O$ and a molecular weight of 438.92. An amount of this drug substance that is equivalent to a specified amount of free base may be calculated by multiplying the specified amount of Compound (I) by 1.2; thus, 38.4 mg of this drug substance is equivalent to 32.0 mg of the free base of Compound (I).

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "isomer" refers to salts and/or compounds that have the same composition and molecular weight but differ in physical and/or chemical properties. The structural difference may be in constitution (geometric isomers) or in the ability to rotate the plane of polarized light (stereoisomers). With regard to stereoisomers, the salts of Compound (I) may have one or more asymmetric carbon atom and may occur as racemates, racemic mixtures and as individual enantiomers or diastereomers.

The disclosure also includes pharmaceutical compositions comprising an effective amount of a disclosed salt of Compound (I) and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The terms "patient" and "subject" are used interchangeably herein, and refer to a mammal, e.g., a human, mouse, rat, guinea pig, dog, cat, horse, cow, pig, or non-human primate, such as a monkey, chimpanzee, baboon or rhesus.

In one embodiment, the subject is a human.

In one embodiment, the subject is a human less than 50 years old.

In one embodiment, the subject is a human less than 40 years old.

In one embodiment, the subject is a human less than 30 years old.

In one embodiment, the subject is a human less than 25 years old.

In one embodiment, the subject is a human less than 21 years old.

In one embodiment, the subject is a human less than 18 years old.

In one embodiment, the subject is a human less than 15 years old.

In one embodiment, the subject is a human less than 30, 29, 28, 27, 26, 25, 24, 23, 22, 21, 20, 19, 18, 17, 16, 15, 14, 13, 12, 11 or 10 years old.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder. For example, treating includes curing or improving at least one negative symptom in a schizophrenic subject. For example, treating includes curing or improving at least one negative symptom in a non-schizophrenic subject. For example, treating includes curing or improving at least one negative symptom in a non-schizophrenic subject suffering from one of the diseases or disorders disclosed herein. For example, for amblyopia, the disorder may be treated by improving vision in the amblyopic eye. For autism, the disorder may be treated by decreasing one or more symptoms of irritability, lethargy, and hyperactivity, inadequate eye contact, and inappropriate speech.

The term "disorder" is used in this disclosure to mean, and is used interchangeably with, the terms disease, condition, or illness, unless otherwise indicated.

The term "administer", "administering", or "administration" as used in this disclosure refers to either directly administering Compound (I), or a salt, hydrate, composition, or dosage form thereof to a subject, or administering a prodrug derivative or analog of Compound (I), or a salt, hydrate, composition, or dosage form thereof to the subject, which can form an equivalent amount of active salt within the subject's body.

An "atypical antipsychotic" includes, without limitation, risperidone, olanzapine, clozapine, quetiapine, ziprasidone, aripiprazole, seritindole, zotepine, and perospirone.

A "typical antipsychotic" includes, without limitation, haloperidol, loxapine, thioridazine, molindone, thiothixene, fluphenazine, mesoridazine, trifluoperazine, perphenazine, and chlorpromazine.

Other examples of agents useful in combination with Compound (I) in any of the methods disclosed herein include, without limitation, fluoxetine, citalopram, escitalopram, venlafaxine, duloxetine, bupropion.

The dosages of Compound (I), a composition comprising Compound (I), or a dosage form comprising Compound (I), for any of the methods and uses described herein vary depending on the agent, the age, weight, and clinical condition of the recipient subject, and the experience and judgment of the clinician or practitioner administering the therapy, among other factors affecting the selected dosage.

The therapeutically effective amount of Compound (I) may be administered one or more times over a day for up to 30 or more days, followed by 1 or more days of non-administration of Compound (I). This type of treatment schedule, i.e., administration of Compound (I) on consecutive days followed by non-administration of Compound (I) on consecutive days may be referred to as a treatment cycle. A treatment cycle may be repeated as many times as necessary to achieve the intended affect.

In one embodiment, the therapeutically effective amount of Compound (I) is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg administered once, twice, three time, four times, or more daily for one, two, three, four, five, six, seven, eight, nine, ten, eleven, twelve, thirteen, fourteen, fifteen, thirty consecutive days, or, once, twice, three time, four times, or more daily for 2 months, 3 months, 4 months, 5 months, 6 months, or longer.

In one embodiment, the therapeutically effective amount of Compound (I) is administered once or twice a day chronically (i.e., indefinitely).

Dosages of Compound (I) can also range from about 0.01 mg/kg per day to about 3000 mg/kg per day. In an aspect, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer.

As used herein, the term "dosage effective manner" refers to amount of Compound (I) to produce the desired biological effect in a subject or cell.

The therapeutically effective amount of Compound (I) can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of Compound (I) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing Compound (I) may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of Compound (I) into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating Compound (I) in the required amount in an appropriate solvent with one or a combination of ingredients enumerated above, as required, followed by filtered sterilization. Generally, dispersions are prepared by incorporating the active agent or compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, Compound (I) can be incorporated with excipients and used in the form of tablets, troches, or capsules. Oral compositions can also be prepared using a fluid carrier for use as a mouthwash, wherein the agent or compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the agents or compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents or compounds are formulated into ointments, salves, gels, or creams as generally known in the art.

In one aspect, Compound (I) is prepared with pharmaceutically acceptable carriers that will protect the agent or compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active agent or compound calculated to produce the desired therapeutic effect in association with the required pharmaceutical carrier. The specification for the dosage unit forms of the application are dictated by and directly dependent on the unique characteristics of Compound (I) and the particular therapeutic effect to be achieved.

In an embodiment, Compound (I) is administered in any of the gastro-resistant, controlled release dosage forms described in US 2019/0038561, which in incorporated herein by reference in its entirety.

The pharmaceutical compositions can include co-formulations of Compound (I) with any of the agents or compounds described herein, including for example a typical or atypical antipsychotic.

The pharmaceutical compositions can be included in a container, pack, or dispenser together with instructions for administration.

The dosage regimen utilizing the disclosed salt is selected in accordance with a variety of factors including type, species, age, weight, sex and medical condition of the patient; the severity of the condition to be treated; the route of administration; the renal or hepatic function of the patient; and the particular disclosed salt employed. A physician or veterinarian of ordinary skill in the art can readily determine and prescribe the effective amount of the drug required to prevent, counter or arrest the progress of the condition.

Illustrative modes of administration for Compound (I) includes systemic or local administration such as oral, nasal, parenteral, transdermal, subcutaneous, vaginal, buccal, rectal or topical administration modes. In one embodiment, Compound (I), or a pharmaceutically acceptable salt or hydrate thereof, is administered orally.

Illustrative pharmaceutical compositions are tablets and gelatin capsules comprising a salt of Compound (I) and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the salt such as cyclodextrin, hydroxypropyl-cyclodextrin, PEG400, and/or PEG200.

For preparing pharmaceutical compositions from Compound (I), or a salt or hydrate thereof, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed salt is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Pharmaceutical compositions can be prepared according to conventional mixing, granulating or coating methods, respectively, and the present pharmaceutical compositions can contain from about 0.1% to about 99%, from about 5% to about 90%, or from about 1% to about 20% of the disclosed salt by weight or volume.

SUMMARY OF EXAMPLES AND RESULTS

Primary cultures of astrocytes were obtained from the cerebral cortex of newborn rats and cultured as described by McCarthy et al., 1980.

At confluency, astrocytes were plated in 96-well Nunc MaxiSorp surface polystyrene flat-bottom immunoplate pre-coated with poly-D-lysine during 30 min. and an anti-BDNF monoclonal antibody overnight at 4° C. at a density of 30,000 cells/well. The procedure was done as described by (Balkowiec and Katz, 2002) and (Malik et al., 2014; Su et al., 2012). Cells were incubated for 5 days with or without the test compound pridopidine at 1 µM as reference compound and Compound (I) at concentrations ranging from 3 nM to 1 µM. At the end of drug treatment, cells were carefully washed with TBST (20 mM Tris-HCl (pH 7.6), 150 mM NaCl, and 0.05% (vol/vol) Tween 20). The plate was then incubated with the polyclonal anti-human BDNF antibody overnight and BDNF quantified.

Primary cultures of hippocampal neurons were obtained from newborn rats (Wistar rats) as described by Balkowiec and Katz (2002). Hippocampal neurons were plated in 96-well Nunc MaxiSorp surface polystyrene flat-bottom immunoplate precoated with poly-D-lysine during 30 min an anti-BDNF monoclonal antibody overnight at 4° C. at a density of 70,000 cells/well. The procedure was done as described by (Balkowiec and Katz, 2002) and (Malik et al., 2014; Su et al., 2012). Cells were incubated for 3 days with or without the test compound pridopidine at 1 µM as reference compound and Compound (I) at concentrations ranging from 3 nM to 1 µM. At the end of drug treatment, cells were carefully washed with TBST (20 mM Tris-HCl (pH 7.6), 150 mM NaCl, and 0.05% (vol/vol) Tween 20). The plate was then incubated with the polyclonal anti-human BDNF antibody overnight and BDNF quantified. In this condition, after 3 days of culture, the hippocampal neurons culture contains less than 5% of astrocytes.

For analysis of BDNF expression by real-time quantitative polymerase chain reaction (qPCR), astrocytes were seeded in 24 well-plates pre-coated with poly-D-lysine. After 1 day of culture, fresh serum free medium containing compounds was added during 5 days at 37° C. At the end of the incubation time total RNA content were extracted and reverse transcription was performed. Expression levels were calculated using the ΔCt method where the expression level of the mRNA of interest is given by 2-ΔCT with ΔCT=CT target mRNA−CT reference mRNA (Gapdh), in the same sample.

It has been found that that Compound (I) has neurotrophic and neuroprotective effects by virtue of enhancing the release and expression of BDNF and the release of Glial-cell derived neurotrophic factor (GDNF) in astrocytes and hippocampal neurons.

Compound (I)'s effects on BDNF release by astrocytes was dose-dependent and the 300 nM dose produced the maximal increase of BDNF release of 29.5% compared to control. The level of BDNF release following the administration of Compound (I) at 300 nM was greater than the effect shown by pridopidine at 1 µm, the reference molecule used in the study. (See Example 1.) Pridopidine is currently under development for Huntington's disease (Pridopidine activates neuroprotective pathways impaired in Huntington's Disease, M. Geva et al, Human Molecular Genetics, 2016, Volume 25 Number 18, doi:10.1093/hmg/ddw238).

Compound (I)'s effects on BDNF release by hippocampal neurons was dose-dependent and the 300 nM dose produced the maximal increase of BDNF release of 27.5% compared to control. The level of BDNF release following the administration of Compound (I) at 300 nM was greater than the effect shown by pridopidine at 1 µm. (See Example 2.)

Compound (I)'s effects on GDNF release by astrocytes was dose-dependent and the 300 nM dose produced the maximal increase of GDNF release of 20.8% compared to control. The level of GDNF release following the administration of Compound (I) at 300 nM was greater than the effect shown by dexmedetomidine at 1 µm, the reference molecule used in the study. (See Example 3.)

Compound (I)'s effects on BDNF expression in rat astrocytes showed a U-dose response pattern and the 3 nM dose produced the maximal increase of BDNF expression of 81% compared to control. Glatiramer acetate only resulted in a 10% increase as a dose of 25 µg/mL. (See Example 4.)

Our present results show that Compound (I) increased BDNF release by astrocytes and hippocampal neurons and GDNF release by astrocytes. Moreover, Compound (I) is able to enhance the expression of BDNF at drug concentrations similar to those observed in human at tested doses. These findings, along with the clinical results seen during the phase 2b study, suggest the potential of Compound (I) to change the overall course of schizophrenia and other psychiatric disorders. Moreover, in addition to the known neurotransmitter pathways targeted by Compound (I), particularly on the serotoninergic 5-$HT_{2A}$ and the sigma2 pathways, the effect of Compound (I) on BDNF and GDNF suggests that Compound (I) may have the potential for disease modification and improved neuroplasticity.

Negative Symptoms

Negative symptoms generally refer to a reduction in normal functioning, and include five major sub-domains: blunted affect (affective flattening, blunted expression), alogia (poverty of speech), amotivation (loss of volition), anhedonia (reduced ability to experience or anticipate pleasure) and asociality (social withdrawal). While negative symptoms are a well-documented and intensively studied aspect of schizophrenia, this class of symptoms has been identified in patients with other disorders, including, for example, Alzheimer's disease and other dementias, particularly frontotemporal dementia (FTD), autism spectrum disorder (ASD), bipolar disorder (BPD), major depressive disorder (MDD), Parkinson's disease, temporal lobe epilepsy, stroke, and traumatic brain injury (TBI) (see, e.g., Boone et al, J. of Internat. Neuropsycol. Soc., 2003, Vol 9, pages 698-709; Bastiaansen, J. et al., J. Autism Dev. Disord. 2011, Vol 41:1256-1266; Getz, K. et al., Am. J. Psychiatry 2002, Vol 159:644-651; Winograd-Gurvich, C. et al., Brain Res. Bulletin, 2006, Vol. 70:312-321; Galynker et al., Neuropsychiatry Neuropsychol. Behav. Neurol. 2000, Vol 13:171-176; Galynker I, et al., J. Nerv. Ment. Dis 1997, Vol 185:616-621; Chaudhury, S., et al., Indian J. of Neurotrauma 2005, Vol 2:13-21; Ameen, S et al., German J. of Psychiatry 2007).

Indeed, it was proposed that negative symptoms are common to mental illnesses generally (Herbener and Harrow, Schizophrenia Bulletin 2001, Vol. 27:527-537).

Furthermore, reports of several population studies have concluded that between 20-22% of the general population have one or more negative symptoms, and that the majority of subjects with negative symptoms do not exhibit a clinical diagnosed psychiatric disorder (Werbeloff, N. et al., PLoS ONE 2015, Vol 10:e0119852; Barrantes-Vidal, N., et al., Schizophr. Res. 2010, Vol 122:219-225).

In one embodiment, the negative symptom is anhedonia, blunted affect, emotional withdrawal, poor rapport, passive/apathetic social withdrawal, difficulty in abstract thinking, lack of spontaneity or flow of conversation, or stereotyped thinking.

While positive symptoms represent the presence of something not normally experienced, negative symptoms reflect the absence of thoughts and behaviors that would otherwise be expected and thus reflect a decrease or loss of normal function or the loss or absence of normal behaviors.

One aspect of this application is method of treating or diminishing at least one negative symptom in a subject, comprising administering a therapeutically effective amount of Compound (I), or a pharmaceutically acceptable salt or hydrate thereof, a composition thereof, or a dosage form thereof, to the subject.

In one embodiment, the administration of Compound (I) starts before the manifestation of a first positive symptom.

In one embodiment, the administration of Compound (I) starts concurrently with the manifestation of a first positive symptom.

In one embodiment, the subject in need of treatment of a negative symptom is schizophrenic.

In one embodiment, the subject in need of treatment of a negative symptom is non-schizophrenic.

In one embodiment, the subject in need of treatment of a negative symptom has not been diagnosed with a psychiatric disorder.

In one embodiment, the subject in need of treatment of a negative symptom suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

The negative symptom is one of the five major sub-domains of negative symptoms: blunted affect, alogia, amotivation, anhedonia and asociality. The core characteristics of each sub-domain are described below.

Blunted affect (affective flattening, blunted expression) is characterized by reduced intensity and range of emotional expression as manifested via vocal and non-verbal modes of communication including intonation (prosody), facial expression, hand-gestures and body movements.

Alogia (poverty of speech) is characterized by decreased quantity of speech, reduced spontaneous speech and loss of conversational fluency.

Amotivation (loss of volition) is characterized by deficits in the initiation and maintenance of goal-directed behaviors like work, study, sport, personal hygiene and daily tasks, especially when requiring and effort (cognitive or physical) and significant organization, as well as deficits in desire to undertake such activities. This sub-domain is related to apathy and lack of energy.

Anhedonia (reduced ability to experience or anticipate pleasure) is characterized by the looking forward to a reward, recreational or other pleasurable experience ("wanting") being more markedly and consistently impaired (anticipatory anhedonia) than the appreciation ("liking") of the experience itself (consummatory anhedonia).

Asociality (social withdrawal) is characterized by diminished interest in, motivation for, and appreciation of social interactions with others, like family and friends, loss of interest in intimate (sexual) relationships independent of any somatic problems, and for a child, may include loss of interest in playing with other children.

One aspect of this application is method of treating or diminishing blunted affect, affective flattening, or blunted expression in a subject, comprising administering a therapeutically effective amount of Compound (I), or a pharmaceutically acceptable salt or hydrate thereof, a composition thereof, or a dosage form thereof, to the subject. In one embodiment, the administration of Compound (I) starts before the manifestation of a first positive symptom. In one embodiment, the administration of Compound (I) starts concurrently with the manifestation of a first positive symptom.

In one embodiment, the subject in need of treatment of blunted affect, affective flattening, or blunted expression is schizophrenic.

In one embodiment, the subject in need of treatment of blunted affect, affective flattening, or blunted expression is non-schizophrenic.

In one embodiment, the subject in need of treatment of blunted affect, affective flattening, or blunted expression has not been diagnosed with a psychiatric disorder.

In one embodiment, the subject in need of treatment of blunted affect, affective flattening, or blunted expression suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application is method of treating or diminishing alogia in a subject, comprising administering a therapeutically effective amount of Compound (I), or a pharmaceutically acceptable salt or hydrate thereof, a composition thereof, or a dosage form thereof, to the subject. In one embodiment, the administration of Compound (I) starts before the manifestation of a first positive symptom. In one embodiment, the administration of Compound (I) starts concurrently with the manifestation of a first positive symptom.

In one embodiment, the subject in need of treatment of alogia is schizophrenic.

In one embodiment, the subject in need of treatment of alogia is non-schizophrenic.

In one embodiment, the subject in need of treatment of alogia has not been diagnosed with a psychiatric disorder.

In one embodiment, the subject in need of treatment of alogia suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application is method of treating or diminishing amotivation in a subject, comprising administering a therapeutically effective amount of Compound (I), or a pharmaceutically acceptable salt or hydrate thereof, a composition thereof, or a dosage form thereof, to the subject. In one embodiment, the administration of Compound (I) starts before the manifestation of a first positive symptom. In one embodiment, the administration of Compound (I) starts concurrently with the manifestation of a first positive symptom.

In one embodiment, the subject in need of treatment of amotivation is schizophrenic.

In one embodiment, the subject in need of treatment of amotivation is non-schizophrenic.

In one embodiment, the subject in need of treatment of amotivation has not been diagnosed with a psychiatric disorder.

In one embodiment, the subject in need of treatment of amotivation suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application is method of treating or diminishing anhedonia in a subject, comprising administering a therapeutically effective amount of Compound (I), or a pharmaceutically acceptable salt or hydrate thereof, a composition thereof, or a dosage form thereof, to the subject. In one embodiment, the administration of Compound (I) starts before the manifestation of a first positive symptom. In one embodiment, the administration of Compound (I) starts concurrently with the manifestation of a first positive symptom.

In one embodiment, the subject in need of treatment of anhedonia is schizophrenic.

In one embodiment, the subject in need of treatment of anhedonia is non-schizophrenic.

In one embodiment, the subject in need of treatment of anhedonia has not been diagnosed with a psychiatric disorder.

In one embodiment, the subject in need of treatment of anhedonia suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

One aspect of this application is method of treating or diminishing asociality in a subject, comprising administering a therapeutically effective amount of Compound (I), or a pharmaceutically acceptable salt or hydrate thereof, a composition thereof, or a dosage form thereof, to the subject. In one embodiment, the administration of Compound (I) starts before the manifestation of a first positive symptom. In one embodiment, the administration of Compound (I) starts concurrently with the manifestation of a first positive symptom.

In one embodiment, the subject in need of treatment of asociality is schizophrenic.

In one embodiment, the subject in need of treatment of asociality is non-schizophrenic.

In one embodiment, the subject in need of treatment of asociality has not been diagnosed with a psychiatric disorder.

In one embodiment, the subject in need of treatment of asociality suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

The severity of negative symptoms, as well as the worsening or improvement of these symptoms, may assessed by any of the various medical scales known in the art. For example, the Positive and Negative Syndrome Scale (PANSS) and the Scale for the Assessment of Negative Symptoms (SANS). A detailed description of PANSS is included in US 2019/0216793, which is incorporated by reference herein.

Positive Symptoms

Positive symptoms in schizophrenia and other psychiatric and neurological disorders, including the ones disclosed herein, may involve the experience of something in consciousness that should not normally be present. For example, hallucinations and delusions represent perceptions or beliefs that should not normally be experienced. In addition to hallucinations and delusions, patients with schizophrenia frequently have marked disturbances in the logical process of their thoughts. Specifically, psychotic thought processes are characteristically loose, disorganized, illogical, or bizarre. These disturbances in thought process frequently produce observable patterns of behavior that are also disorganized and bizarre. The severe disturbances of thought content and process that comprise the positive symptoms often are the most recognizable and striking features of schizophrenia and other psychiatric and neurological disorders.

In one embodiment, a positive symptom as referred to herein, comprises a hallucination, delusion, disorganized thinking, movement disorder, or depersonalization. In one embodiment, the subject suffering from the positive symptom is schizophrenic. In one embodiment, the subject suffering from the positive symptom is non-schizophrenic. In one embodiment, the subject suffering from the positive symptom has not been diagnosed with a psychiatric disorder. In one embodiment, the subject suffering from the positive symptom also suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

The severity of positive symptoms, as well as the worsening or improvement of these symptoms, may assessed by any of the various medical scales known in the art. For example, the Positive and Negative Syndrome Scale (PANSS) and the Scale for the Assessment of Positive Symptoms (SANS). A detailed description of PANSS is included in US 2019/0216793, which is incorporated by reference herein.

Neuroplasticity

Neuroplasticity (also referred to as brain plasticity or cortical plasticity) is the ability of the nervous system to change or respond to intrinsic or extrinsic stimuli by reorganizing its structure, function and connections. Neuroplasticity is thought to be a cellular mechanism underlying learning and memory (Harnessing neuroplasticity for clinical applications. Cramer, S. C. et al. Brain. 2011; 134 (Pt. 6): 1591-609). Neuroplasticity is the process that underlies neurogenesis and plays a pivotal role in learning and memory processes. Studies have been performed on the molecular and cellular mechanisms underlying neural plasticity responses in learning and memory, as well as anxiety, depression, allodynia, neuropathic pain and drug abuse, some of the most exciting areas of research in neuroscience (Enciu, A. M. et al. BMC Neurology 2011, 11: 75; Caroni, P. et al. Nat Rev Neurosci 2012, 13(7): 478-90; Carlson, P. J. et al. NeuroRx 2006, 3(1): 22-41; Disner, S. G. et al. Nat Rev Neurosci 2011, 12(8): 467-77; Latremoliere, A. and Woolf, C. J. J Pain 2009, 10(9): 895-26; Madsen, H. B. et al. Front. Mol. Neurosci. 2012, 5: 99). BDNF has also been demonstrated to play a role as mediator of neuroplasticity in bipolar disorder (Grande, I. et al. Psychiatry Investig. 2010; 7(4): 243-250.)

Neuroplastic changes have been observed in a large variety of diseases, such as Alzheimer's disease; amyotrophic lateral sclerosis; Angelman syndrome; Asperger syndrome; autistic disorders; bipolar disorder; brain injury; Creutzfeldt-Jakob disease; depression; Down syndrome; epilepsy; fragile X syndrome; Friedrich's ataxia; frontotemporal dementia; frontotemporal lobar degeneration; Huntington's disease; Lewy body disease; multiple sclerosis; multiple system atrophy; Parkinson's disease; Pick's disease; post-traumatic stress disorders; prion disorders; Rett syndrome; schizophrenia; spinal and bulbar muscular atrophy; spinal cord injuries; spinocerebellar ataxias; stroke; supranuclear palsy; progressive and tuberous sclerosis.

Pharmacotherapies to increase neuroplasticity through molecular manipulation of different cellular and synaptic pathways are needed, since at present only modest or small benefits have been achieved in the treatment of the diseases disclosed herein.

Compound (I) is shown herein to significantly increase the release of BDNF and GDNF in rat astrocytes and cultured brain hippocampal neurons in a dose dependent manner. Compound (I) is also shown to enhance BDNF expression in rat astrocytes. This activity makes Compound (I) a promising candidate as a neuroplasticity promoter useful in the enhancement of memory consolidation and learning and in diseases and/or disorders associated with cognitive deficits, including, for example, any of the diseases disclosed herein.

One aspect of this application is the use of the Compound (I), a composition thereof, or a dosage form thereof in a method for promoting or increasing neuroplasticity in a subject in need thereof. In one embodiment, the subject is schizophrenic. In one embodiment, the subject is non-schizophrenic. In one embodiment, the subject has not been diagnosed with a psychiatric disorder. In one embodiment, the subject suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

Neuroprotection

Neuroprotection is the relative preservation of neuronal structure and/or function. (Casson et al. Clinical and Experimental Ophthalmology, 2012, 40(4): 350-57.)

Compound (I) is shown herein to significantly increase the release of BDNF and GDNF in rat astrocytes and cultured brain hippocampal neurons in a dose dependent manner. Compound (I) is also shown to enhance BDNF expression in rat astrocytes. This activity makes Compound (I) a promising candidate as a neuroprotective promoter, useful in the enhancement of memory consolidation and learning and in diseases and/or disorders associated with cognitive deficits, including, for example, any of the diseases disclosed herein.

One aspect of this application is the use of the Compound (I), a composition thereof, or a dosage form thereof in a method or promoting neuroprotection in a subject in need thereof. In one embodiment, the method comprises contacting Compound (I) with a neuronal cell, wherein said contacting prevents or delays neuronal cell death relative to neuronal cell death occurring in the absence of said contacting. In one embodiment, the contacting promotes nerve regeneration by stimulating neuronal growth. In one embodiment, the subject is schizophrenic. In one embodiment, the subject is non-schizophrenic. In one embodiment, the subject has not been diagnosed with a psychiatric disorder. In one embodiment, the subject suffers from amblyopia, autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

As used herein, the term "promotes neuroprotection" refers to conditions under which neuronal cell death (necrotic, apoptotic or otherwise) is prevented or decreased, e.g., by at least 20%, at least 30%, at least 40%, at least 50%, at least 60%, at least 75%, at least 90%, at least 95% or more, up to and including, 100% (complete protection) in the presence of Compound (I) or a salt, solvate, or composition thereof, relative to the absence of Compound (I) or a salt, solvate, or composition thereof. In one embodiment, neuronal cell death is decreased at least 2 times, at least 5 times, at least 10 times, at least 15 time, at least 20 times, or more in the presence of Compound (I) or a salt, solvate, or composition thereof, relative to the absence of Compound (I) or a salt, solvate, or composition thereof.

In one embodiment, the term "promotes neuroprotection" also refers to conditions under which neuronal cell growth, axonal elongation, neuronal proliferation or functional organization is increased by at least 20%, at least 30%, at least 40%, at least 50%, at least 60%, at least 75%, at least 90%, at least 95% or more, up to and including, for example, at least 1 times, at least 2 times, at least 3 times, at least 5 times, at least 10 times, at least 20 times or more in the presence of Compound (I) or a salt, solvate, or composition thereof relative to the absence of Compound (I) or a salt, solvate, or composition thereof.

Effects of neuroprotection can be assessed by any assay known in the art, e.g., neural cell death, neural outgrowth, or as described in U.S. Pat. No. 10,286,032, which is incorporated by reference herein.

Learning & Memory Disorders

Compound (I) is shown herein to significantly increase the release of BDNF and GDNF in rat astrocytes and cultured brain hippocampal neurons in a dose dependent manner. Compound (I) is also shown to enhance BDNF expression in rat astrocytes. This activity makes Compound (I) a promising candidate for the enhancement of memory consolidation and learning and for use in the treatment of diseases and/or disorders associated with cognitive deficits, including, for example, in the treatment of nervous system diseases and/or the treatment of developmental, behavioral and/or mental disorders associated with cognitive deficits, particularly learning and memory disorders. Non-limiting examples of such diseases and/or disorders are Down syndrome, Angelman syndrome, Rett syndrome, autistic disorders, fragile X disorder Asperger syndrome, depression, bipolar disorder, schizophrenia, cerebral dementias post-traumatic stress disorders, Pick's disease and sleep disorders, amyotrophic lateral sclerosis, frontotemporal dementia and Friedrich's ataxia, neuropathic, Alzheimer's disease, Parkinson's disease, Huntington's disease, autistic disorders, Down syndrome, fragile X syndrome and Rett syndrome.

Amblyopia

Amblyopia is a condition of the visual system in which one eye fails to develop a normal level of visual acuity during the developmental period for vision. Amblyopia can occur in subjects who are strabismic (have a squint) or have anisometropia (such that both eyes have different refractive errors, leaving one eye defocused), or a combination of both (mixed amblyopia). Amblyopia can also arise from stimulus deprivation (for example, as a result of having a cataract). The poor vision resulting from amblyopia does not always resolve even when the underlying condition has been treated.

Amblyopia is a common condition of childhood, affecting perhaps as many as 2-3 percent of the population, and can carry over into adult life if left untreated. Whilst most people can manage with a lazy eye, they may well have reduced or no binocular function and this may compromise their ability to perform certain complex tasks, such as flying an airplane or driving a train. Furthermore, persons with one amblyopic eye who suffer injury to their "normal" eye may be effectively blind.

A person's visual field can be divided into peripheral and central vision. In amblyopia, the peripheral vision is normal but there is a defect in the central vision with reduced sensitivity to detection of stimuli with high spatial frequency, which is reflected in reduced visual acuity, and the presence of a central area of reduced visual sensitivity (scotoma).

Compound (I) is shown herein to significantly increase the release of BDNF and GDNF in rat astrocytes and cultured brain hippocampal neurons in a dose dependent manner. Compound (I) is also shown to enhance BDNF expression in rat astrocytes. This activity makes Compound (I) a promising candidate for the treatment of amblyopia.

In one aspect, this application pertains to a method of treating amblyopia in a subject in need thereof comprising administering a therapeutically effective amount of Compound (I) or a pharmaceutically acceptable salt or hydrate thereof, or a composition or dosage form thereof. In one embodiment, the subject is also schizophrenic. In one embodiment, the subject is non-schizophrenic. In one embodiment, the subject has not been diagnosed with a psychiatric disorder. In one embodiment, the subject also suffers from autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

Autism Disorders

Autism disorders are severe neurobehavioral syndromes understood to be inherited disorders, although environmental factors are thought to contribute in at least some autism disorders. Autism disorders typically cause major defects in perception, cognition, executive functions and motor control. Although these effects differ between types of autism, abnormalities in language and social skills are pervasive throughout types of autism disorders.

The underlying mechanisms of autism disorders are poorly understood, but a hypothesis has gained favor that autism disrupts neural systems by causing an abnormal balance of the ratio of excitation to inhibition, possibly associated with chronically elevated neuronal activity without cell death. For example, Fragile X syndrome is a type of autism disorder arising from mutations in an untranslated region of the FMR1 gene on the X chromosome. This gene encodes a protein required for normal neural development, and the mutations prevent expression of this protein.

Compound (I) is shown herein to significantly increase the release of BDNF and GDNF in rat astrocytes and cultured brain hippocampal neurons in a dose dependent manner. Compound (I) is also shown to enhance BDNF expression in rat astrocytes. This activity makes Compound (I) a promising candidate for the treatment of autism disorders.

In one aspect, this application pertains to a method of treating an autism disorder in a subject in need thereof comprising administering a therapeutically effective amount of Compound (I) or a pharmaceutically acceptable salt or hydrate thereof, or a composition or dosage form thereof.

In one embodiment, the autism disorder is classic autism, Asperger's syndrome, childhood disintegrative disorder, Rett syndrome, pervasive developmental disorders—not otherwise specified, fragile X syndrome, and combinations thereof. In one embodiment, the subject is also schizophrenic. In one embodiment, the subject is non-schizophrenic. In one embodiment, the subject has not been diagnosed with a psychiatric disorder. In one embodiment, the subject also suffers from mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, (neuroleptic-induced) deficit syndrome, arachnoid cysts, bipolar disorder, catalepsy, encephalitis, Huntington's disease, infections (e.g. meningitis), locked-in syndrome, migraines, multiple sclerosis, myelopathy, or Tourette's syndrome.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1. Effect of Compound (I) on BDNF Release in Rat Astrocytes

Experimental Protocol—In Situ ELISA on Primary Astrocytes Rat Primary Culture of Astrocytes Rat mixed glial cells were cultured as described by McCarthy et al. Primary rat glial cells were prepared from the cortical of newborn Wistar rats (1 day). Briefly, meninges and blood vessels of the mice cortex were removed and placed in ice-cold medium of Leibovitz (L15; PanBiotech, ref P04-27055, batch 4511117) containing 2% Penicillin-Streptomycin (PS; PanBiotech, ref P06-07100, batch 2110917) and 1% of bovine serum albumin (BSA; PanBiotech, ref P10-023100, batch, 9610717) at 37° C. for 10 min.) Tissues were dissociated with 0.25% trypsin-EDTA (PanBiotech, ref P10-023100, batch 8970318) at 37° C. for 10 min. Cells were then submitted to a supplementary incubation of 15 min. at 37° C. in presence of deoxyribonuclease I (0.1 mg/mL Panbiotech, ref: P60-37780100, batch: H140508). Cells were then pelleted (5 min. at 1200 rpm) and trypsinization was stopped by adding DMEM (PanBiotech, Ref P04-03600, Batch 8420517) supplemented with 10% FCS (Fischer, Ref 10270106, batch 41A0940K), 1 mM of Na/pyruvate (PanBiotech, ref: P04-43100, batch 3470914). Cells suspension was mechanically dissociated and filtered through 40 µM diameter nylon meshes (BD Falcon, Ref: 352340).

The cells were collected by centrifugation at 1200 rpm/min for 10 min, resuspended in culture medium and then plated in culture flasks (Dutscher, ref: 690175). Cells were seeded at a density of $1.25 \times 10^5$ cells/cm$^2$ and culture in 5% $CO_2$ at 37° C. Medium was changed 3 times per week.

At confluency, astrocytes were plated in 96-well Nunc MaxiSorp surface polystyrene flat-bottom immunoplate precoated with poly-D-lysine during 30 min (Sigma, Ref: P7886, batch: SLBS8705) and an anti-BDNF monoclonal antibody overnight at 4° C. at a density of 30,000 cells/well. (Balkowiec and Katz "Cellular Mechanisms Regulating Activity-Dependent Release of Native Brain-Derived Neurotrophic Factor from Hippocampal Neurons" J. Neuroscience (2002) 22(23):10399-10407; Malik M., et al. "The Effects of Sigma-1 Receptor Selective Ligands on Muscarinic Receptor Antagonist Induced Cognitive Deficits in Mice" Br J of Pharmacology, (2015) 172(10):2519-31; Su, C. et al. "Progesterone increases the release of brain-derived neurotrophic factor from glia via progesterone receptor membrane component 1 (Pgrmc1)-dependent ERK5 signaling", Endocrinology (2012) 153(9):4389-4400. After 2 hours incubation with culture medium to remove any residue of the ELISA washing solution and incubation to ensure cell attachment to the plate, cells were incubated under the following conditions:

Astrocytes incubated 5 days with control medium
Astrocytes incubated 5 days with Compound (I) at 1 µM, 300 nM, 100 nM, 30 nM, and 10 nM.
Astrocytes incubated 5 days with pridopidine at 1 µM.

At the end of drug treatment, cells were carefully washed with TBST (20 mM Tris-HCl (pH 7.6), 150 mM NaCl, and 0.05% (vol/vol) Tween 20). The plate was then incubated with the polyclonal anti-human BDNF antibody overnight. The amount of specifically bound polyclonal antibody, which when exposed to chromogenic substrate (TMB reagent; Promega), changes color in proportion to the amount of BDNF present in the sample. The color intensity was quantified by measuring the absorbance at 450 nm. BDNF standards, ranging in concentration from 0 to 500 pg/mL were added in parallel wells in the same medium than hippocampal neurons.

Results

The in situ ELISA test based on cultured astrocytes showed pridopidine increased BDNF release by 22% compared to control condition BDNF level of 54 pg/mL ($p<0.001$).

Figure 1:
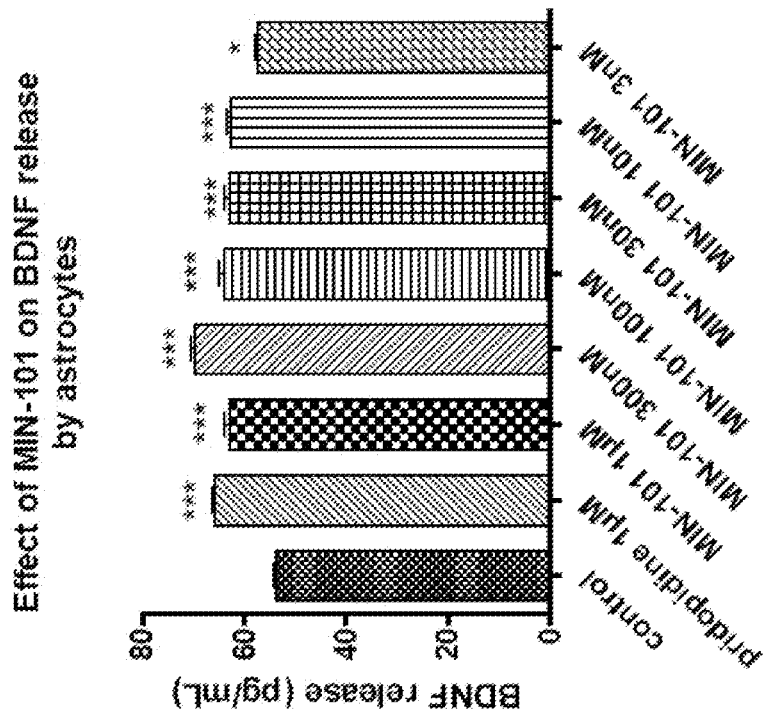
FIG. 1: Effect of Compound (I) on BDNF release by primary rat astrocytes measured by in situ ELISA. Data are expressed in pg/mL (mean±standard error of the mean (sem); *$p<0.05$; $p<0.01$; *$p<0.001$; one way ANOVA followed by Dunnett's test).

Compound (I)'s effects were dose-dependent through the first 5 doses and the 300 nM dose produced the maximal increase of BDNF release of 29.5% compared to control ($p<0.001$). The results of other doses of Compound (I) showed the following increases in BDNF release: 16.9% for 1 µM, 18.9% for 100 nM, 17.1% for 30 nM, 16.2% for 10 nM, all at $p<0.001$. At concentration of 3 nM of Compound, a 6.8% increase ($p<0.05$) was observed. See FIG. 1 and Table 1 for summary.

TABLE 1

| | Effect of Compound (I) on BDNF release by astrocytes (expressed as % increase of control conditions) | | | | | | |
|---|---|---|---|---|---|---|---|
| | Pridopidine | Compound (I) | | | | | |
| Culture | 1 µM | 1 µM | 300 nM | 100 nM | 30 nM | 10 nM | 3 nM |
| BDNF release astrocytes | 22.3% | 16.9% | 29.5% | 18.9% | 17.1% | 16.2% | 6.8% |

Example 2. Effect of Compound (I) on BDNF Release in Primary Hippocampal Neurons Experimental Protocol—In Situ ELISA on Primary Hippocampal Neurons Hippocampal Neuron Culture Rat hippocampal neurons were cultured as described by Balkowiec and Katz (2002). Newborn rats (Wistar rats, Janvier) were deeply anesthetized by hypothermia and decapitated. Hippocampi were rapidly and aseptically dissected from each brain in ice-cold medium of Leibovitz (L15, Panbiotech, Ref. P04-27055, batch: 4511117), followed by removal of meninges and mincing to small pieces. The hippocampal tissues were next digested by trypsinization (Trypsin EDTA 1×; PanBiotech, ref P10-023100, batch 9610717) for 20. min at 37° C. The reaction was stopped by the addition of DMEM (Panbiotech, Ref P04-03600, batch: 8420517) containing DNAase I grade II (0.1 mg/ml Panbiotech, ref: P60-37780100, batch: H140508) and 10% of fetal calf serum (FCS, Invitrogen, ref: 10270-098, batch 41A0940K). Cells were mechanically dissociated by 3 passages through a 10 ml pipette. Cells were then centrifuged at 515×g for 10 min at 4° C. The supernatant was discarded and the cells of pellet was re-suspended in a defined culture medium consisting of Neurobasal (Nb, Invitrogen, ref 21103049, batch 1921829) supplemented with 2% of B27 (Invitrogen, ref 17504-044, batch: 11530536), 2 mM of L-glutamine (PanBiotech, ref P04-80100, batch: 8440517), 2% of PS solution and 5 ng/ml human recombinant basic fibroblast growth factor (bFGF, Peprotech, Ref: 100-18B, batch: 021608 C2216). Viable cells were counted in a Neubauer cytometer using the trypan blue exclusion test.

Hippocampal neurons were plated in 96-well Nunc MaxiSorp surface polystyrene flat-bottom immunoplate pre-coated with poly-D-lysine during 30 min (Sigma, Ref: P7886, batch: SLBS8705) an anti-BDNF monoclonal antibody overnight at 4° C. at a density of 70000 cells/well. The procedure was done as described by (Balkowiec and Katz, 2002) and (Malik et al., 2014; Su et al., 2012). After 2 hours incubation with culture medium to remove any residue of the ELISA washing solution and incubation to ensure cell attachment to the plate, ce cells were incubated under the following conditions:

Hippocampal neurons incubated 3 days with control medium
Hippocampal neurons incubated 3 days with Compound (I) at 1 μM, 300 nM, 100 nM, 30 nM, and 10 nM.
Hippocampal neurons incubated 3 days with pridopidine at 1 μM.

At the end of drug treatment, cells were carefully washed with TBST (20 mM Tris-HCl (pH 7.6), 150 mM NaCl, and 0.05% (vol/vol) Tween 20). The plate was then incubated with the polyclonal anti-human BDNF antibody overnight. The amount of specifically bound polyclonal antibody was then detected through the use of the anti-IgY-horseradish peroxidase tertiary antibody, which when exposed to the chromogenic substrate (TMB reagent; Promega), changes color in proportion to the amount of BDNF present in the sample. The color intensity was quantified by measuring the absorbance at 450 nm. (In this condition, after 3 days of culture, the hippocampal neurons culture contains less than 5% of astrocytes.) BDNF standards, ranging in concentration from 0 to 500 pg/ml were added in parallel wells in the same medium than hippocampal neurons.

Results

The in situ ELISA test based on cultured hippocampal neurons showed BDNF release following incubation with pridopidine resulted in 18.4% increase in BDNF release compared to the control condition BDNF level of 178 pg/mL (p<0.001). In this assay, Compound (I)'s effects were dose-dependent through the first 5 doses and reached a plateau at 300 nM with a maximal increase of BDNF release of 27.5% compared to control (p<0.001). The results of other doses of Compound (I) showed the following increases in BDNF release: 24.3% for 1 μM (p<0.001), 14.9% for 100 nM (p<0.001), 11.0% for 30 nM (p<0.05). The 10 nM and 3 nM doses of Compound (I) showed no statistically significant increases in BDNF release. See FIG. 2 and Table 2 for summary.

TABLE 2

Effect of Compound (I) on BDNF release by hippocampal neurons (expressed as % increase of control conditions)

| Culture | Pridopidine | Compound (I) | | | | | |
|---|---|---|---|---|---|---|---|
| | 1 μM | 1 μM | 300 nM | 100 nM | 30 nM | 10 nM | 3 nM |
| BDNF release hippocampal neurons | 18.4% | 24.3% | 27.5% | 14.9% | 11.0% | 1.8% | 0.4% |

Example 3. Effect of Compound (I) on GDNF Release in Astrocytes

Experimental Protocol—In Situ ELISA on Primary Astrocytes

Rat Primary Culture of Astrocytes

Rat mixed glial cells were cultured as described by McCarthy et al. Primary rat glial cells were prepared from the cortical of newborn Wistar rats (1 day). Briefly, meninges and blood vessels of the mice cortex were removed and placed in ice-cold medium of Leibovitz (L15; PanBiotech, ref P04-27055, batch 4511117) containing 2% Penicillin-Streptomycin (PS; PanBiotech, ref P06-07100, batch 2110917) and 1% of bovine serum albumin (BSA; PanBiotech, ref P10-023100, batch, 9610717) at 37° C. for 10 min.) Tissues were dissociated with 0.25% trypsin-EDTA (PanBiotech, ref P10-023100, batch 8970318) at 37° C. for 10 min. Cells were then submitted to a supplementary incubation of 15 min. at 37° C. in presence of deoxyribonuclease I (0.1 mg/mL Panbiotech, ref: P60-37780100, batch: H140508). Cells were then pelleted (5 min. at 1200 rpm) and trypsinization was stopped by adding DMEM (PanBiotech, Ref P04-03600, Batch 8420517) supplemented with 10% FCS (Fischer, Ref 10270106, batch 41A0940K), 1 mM of Na/pyruvate (PanBiotech, ref: P04-43100, batch 3470914). Cells suspension was mechanically dissociated and filtered through 40 μM diameter nylon meshes (BD Falcon, Ref: 352340).

The cells were collected by centrifugation at 1200 rpm/min for 10 min, resuspended in culture medium and then plated in culture flasks (Dutscher, ref: 690175). Cells were seeded at a density of $1.25 \times 10^5$ cells/cm² and culture in 5% $CO_2$ at 37° C. Medium was changed 3 times per week.

At confluency, astrocytes were plated in 96-well Nunc MaxiSorp surface polystyrene flat-bottom immunoplate pre-coated with poly-D-lysine during 30 min (Sigma, Ref: P7886, batch: SLBS8705) and an anti-GDNF monoclonal antibody overnight at 4° C. at a density of 30,000 cells/well.

After 2 hours incubation with culture medium to remove any residue of the ELISA washing solution and incubation to ensure cell attachment to the plate, cells were incubated under the following conditions:

- Astrocytes incubated 5 days with control medium
- Astrocytes incubated 5 days with Compound (I) at 1 µM, 300 nM, 100 nM, 30 nM, and 10 nM.
- Astrocytes incubated 5 days with dexmedetomidine at 1 µM.

At the end of drug treatment, cells were carefully washed with TBST (20 mM Tris-HCl (pH 7.6), 150 mM NaCl, and 0.05% (vol/vol) Tween 20). The plate was then incubated with the polyclonal anti-human GDNF antibody overnight. The amount of specifically bound polyclonal antibody, which when exposed to chromogenic substrate (TMB reagent; Promega), changes color in proportion to the amount of GDNF present in the sample. The color intensity was quantified by measuring the absorbance at 450 nm. GDNF standards, ranging in concentration from 0 to 500 pg/mL were added in parallel wells in the same medium than hippocampal neurons.

Results

Figure 3:
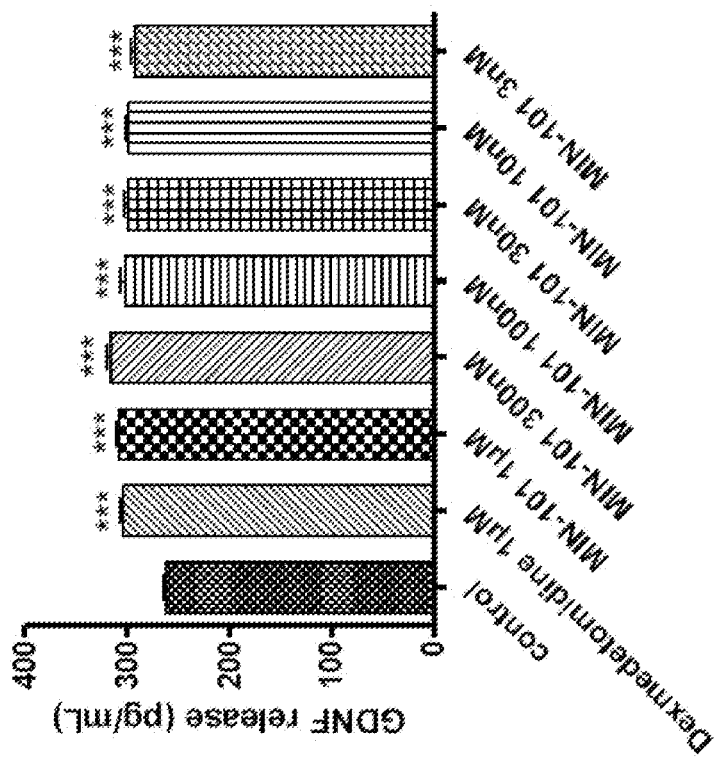
FIG. 3: Effect of Compound (I) on GDNF release by primary rat astrocytes measured by in situ ELISA. Data are expressed in pg/mL (mean±sem; *$p<0.05$; $p<0.01$; *$p<0.001$; one way ANOVA followed by Dunnett's test).

The in situ ELISA test based on cultured astrocytes showed dexmedetomidine increased GDNF release by 15.8% compared to the control condition GDNF level of 262.3 pg/mL (p<0.001). In this assay, Compound (I)'s effects were dose-dependent through the first 5 doses and the 300 nM dose produced the maximal increase of GDNF release of 20.8% compared to control (p<0.001). The results of other doses of Compound (I) showed the following increases in GDNF release: 17.5% for 1 µM, 14.8% for 100 nM, 14.2% for 30 nM, 13.8% for 10 nM (all at p<0.001). At dose of 3 nM of Compound (I) had a 11.4% increase of GDNF release was observed. (p<0.001). See FIG. 3 and Table 3 for summary.

adding DMEM (Panbiotech, Ref P04-03600, Batch 5181217) supplemented with 10% FCS (Fischer, Ref 10270106, batch 42G2068K), 1 mM of Na/pyruvate (PanBiotech, ref: P04-43100, batch: 3470914) and 2% PS. Cells suspension was mechanically dissociated and filtered through 40 µm diameter nylon meshes (BD Falcon, Ref: 352340). The cells were collected by centrifugation at 1200 rpm/min for 10 min, re-suspended in culture medium and then plated in culture flasks (Dutscher, ref: 690175). Cells were seeded at a density of $1.25 \times 10^5$ cells/cm$^2$ and cultured in 5% $CO_2$ at 37° C. Medium was changed three times per week.

Analysis of BDNF expression by real-time quantitative polymerase chain reaction (PCR): astrocytes were seeded in 24 well-plates pre-coated with poly-D-lysine (Sigma, ref P7886, batch: SLBQ9797V). After 1 day of culture, fresh serum free medium containing compounds was added during 5 days at 37° C. At the end of the incubation time, medium was removed and total RNA content were extracted using kit nucleo spin RNS XS (Macherey Nagel; 20 µL/well). 6 wells/condition were done. RNA concentration was determined using a Nanodrop 2000 spectrophotometer (Life Technologies ThermoFisher Scientific, Villebon sur Yvette, France).

Reverse transcription was performed on 500 ng of RNA using the high capacity RNA-to-cDNA mix (Applied Biotechnologies). qPCR was performed on 12.5 ng of cDNA using the following primers, purchased from Applied Biotechnology.

For qPCR reactions, the kit TaqMan™ Fast Universal PCR Master Mix (2×) was used. The following volumes were used: mix: 10 uL, enzyme: 4 uL, oligo: 1 uL each, cDNA: 5 uL (12,5 ng). For the comparisons between various compounds and concentrations, expression levels were calculated using the ΔCt method where the expression level of

TABLE 3

Effect of Compound (I) on GDNF release by astrocytes (expressed as % increase of control conditions)

| Culture | Dexmedetomidine | Compound (I) | | | | | |
|---|---|---|---|---|---|---|---|
| | 1 µM | 1 µM | 300 nM | 100 nM | 30 nM | 10 nM | 3 nM |
| GDNF release astrocytes | 15.8% | 17.5% | 20.8% | 14.8% | 14.2% | 13.8% | 11.4% |

Example 4. Effect of Compound (I) on BDNF Expression in Rat Astrocytes

Experimental Protocol

Rat Primary Culture of Astrocytes—rat mixed glial cells were cultured as described by McCarthy et al., 1980. Primary rat glial cells were prepared from the cortical of newborn Wistar rats (1 day). Briefly, meninges and blood vessels of the mice cortex were removed and placed in ice-cold medium of Leibovitz (L15; PanBiotech, ref P04-27055, batch 4511117) containing 2% of Penicillin-Streptomycin (PS; PanBiotech, ref P06-07100, batch 2110917) and 1% of bovine serum albumin (BSA; PanBiotech, ref P06-1391100, batch H171006). Tissues were dissociated with 0.25% trypsin-EDTA (PanBiotech, ref P10-023100, batch 8970318) at 37° C. for 10 min. Cells were then submitted to a supplementary incubation of 15 min at 37° C. in presence of deoxyribonuclease I (0.1 mg/ml Panbiotech, ref: P60-37780100, batch: H170706). Cells were then pelleted (5 min at 1200 rpm) and trypsinization was stopped by the mRNA of interest is given by 2-ΔCT with ΔCT=CT target mRNA−CT reference mRNA (Gapdh), in the same sample. For the cultures treated with GA or the unknown compound, relative expression levels were determined according to the ΔΔCt method where the expression level of the mRNA of interest is given by 2-ΔΔCT where ΔΔCT=ΔCt for treated cultures−ΔCt for untreated cultures.

The following conditions were done:
- Astroglial cells incubated 5 days with control medium
- Astroglial cells incubated 5 days with Compound (I) at 0.3 nM, 1 nM, 3 nM, 10 nM, 30 nM, 100 nM.
- Astroglial cells incubated 5 days with reference compound (glatiramer acetate, 25 µg/mL, (Reick et al., 2016), Avachem, ref 3822, batch CS1701).

Results

Figure 4:
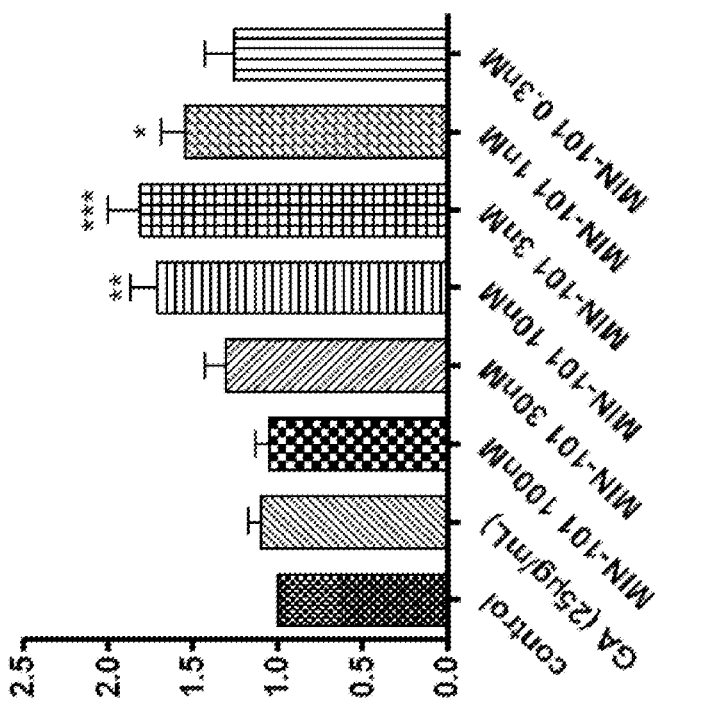
FIG. 4: Effect of Compound (I) on BDNF expression by astrocytes measured by qPCR. Data are expressed in fold change (FC) compared to control condition (mean±sem; *$p<0.05$; $p<0.01$; *$p<0.001$; one way ANOVA followed by Dunnett's test). GA=glatiramer acetate.

Compound (I) at 10 nM, 3 nM and 1 nM increased BDNF expression by astrocytes in a statistical significant manner (, p<0.01, Fc:1.71 at 10 nM, *, p<0.001 Fc: 1.81 at 3 nM and *, p<0.05 Fc:1.55 at 1 nM compared to control condition). In contrast, glatiramer acetate has no effect (ns, p>0.05). See FIG. 4 and Table 4 for summary.

TABLE 4

| | Glatiramer acetate | Compound (I) | | | | | |
|---|---|---|---|---|---|---|---|
| Culture | 25 ug/mL | 100 nM | 30 nM | 10 nM | 3 nM | 1 nM | 0.3 nM |
| BDNF expression astrocytes | 10% | 5% | 31% | 71% | 81% | 55% | 26% |

The qPCR test based on cultured astrocytes showed glatiramer acetate increased BDNF expression by 10% compared to control condition. In this assay, Compound (I)'s effects showed an inverted U dose-response pattern and the 3 nM dose produced the maximal increase of BDNF expression of 81% compared to control (p<0.001). The results of other doses of Compound (I) showed the following increases in BDNF expression: 5% for 100 nM, 31% for 30 nM, 71% for 10 nM (p<0.01), 55% for 1 nM, (p<0.05), and 0.3 nM had a 26% increase.

These results demonstrate that Compound (I) is able to enhance BDNF expression by astrocytes. The maximum efficiency is observed at 3 nM.

Compound (I) enhances the expression of BDNF at drug concentrations similar to those observed in human at tested doses. Therefore, in addition to the known neurotransmitter pathways targeted by Compound (I), particularly on the serotoninergic 5-$HT_{2A}$ and the sigma$_2$ pathways, the effect of Compound (I) on BDNF and GDNF suggests that this compound may have the potential for disease modification and improved neuroplasticity.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The methods of the disclosure have been described herein by reference to certain preferred embodiments. However, as particular variations thereon will become apparent to those skilled in the art, based on the disclosure set forth herein, the disclosure is not to be considered as limited thereto.

Unless otherwise defined, all technical and scientific terms used herein have the same meaning as commonly understood by one of ordinary skill in the art to which this disclosure belongs. In the specification and claims, the singular forms also include the plural unless the context clearly dictates otherwise.

It is to be understood that at least some of the descriptions of the disclosure have been simplified to focus on elements that are relevant for a clear understanding of the disclosure, while eliminating, for purposes of clarity, other elements that those of ordinary skill in the art will appreciate may also comprise a portion of the disclosure. However, because such elements are well known in the art, and because they do not necessarily facilitate a better understanding of the disclosure, a description of such elements is not provided herein.

Further, to the extent that a method does not rely on the particular order of steps set forth herein, the particular order of the steps recited in a claim should not be construed as a limitation on that claim.

All patents, patent applications, references and publications cited herein are fully and completely incorporated by reference as if set forth in their entirety. Such documents are not admitted to be prior art to the present disclosure.

What is claimed is:

1. A method of treating or diminishing amblyopia in a subject in need thereof, comprising administering a therapeutically effective amount of Compound (I),

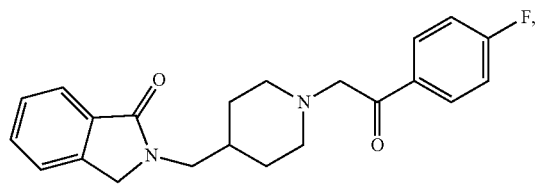 [SMILES: O=C(CN1CCC(CN2Cc3ccccc3C2=O)CC1)c1ccc(F)cc1]

or a pharmaceutically acceptable salt or hydrate thereof, to the subject.

2. The method of claim 1, wherein the administration of Compound (I) increases neuroplasticity in the subject compared with a subject not administered Compound (I), or a pharmaceutically acceptable salt or hydrate thereof.

3. The method of claim 1, wherein the administration of Compound (I) promotes neuroprotection or neural regeneration in the subject compared with a subject not administered Compound (I), or a pharmaceutically acceptable salt or hydrate thereof.

4. The method of claim 1, wherein the therapeutically effective amount of Compound (I) is administered to the subject once or twice daily for 1 month, 2 months, 3 months, 4 months, 5 months, 6 months, or longer.

5. The method of claim 1, wherein the subject is also administered an antipsychotic.

6. The method of claim 1, wherein the subject is less than 50, 40, 30, 25, 20, 19, 18, 17, 16, 15, 14, 13, 12, or 11 years old.

7. The method of claim 1, wherein the subject is strabismic.

8. The method of claim 1, wherein the subject is anisometric.

9. The method of claim 1, wherein the subject is schizophrenic.

10. The method of claim 1, wherein the subject is non-schizophrenic.

11. The method of claim 1, wherein the subject has not been diagnosed with a psychiatric disorder.

12. The method of claim 1, wherein the subject also suffers from an autism disorder, mental retardation, organic personality disorder, antisocial personality disorder, schizoaffective disorder, schizophreniform disorder, schizoid personality disorder, post-traumatic stress disorder, schizotypal personality disorder, paranoid personality disorder, histrionic personality disorder, narcissistic personality disorder, dependent personality disorder, avoidant personality disorder, somatoform disorder, obsessive compulsive disorder, generalized anxiety disorder, social anxiety disorder, separation anxiety disorder, reactive attachment disorder, panic disorder, depersonalization disorder, derealization disorder, phobia, adjustment disorder, affective disorder, premenstrual dysphoric disorder, selective mutism, obsessive compulsive personality disorder, traumatic brain injury, neuroleptic-induced deficit syndrome, arachnoid cysts, bipolar disorder, catalepsy, encephalitis, Huntington's disease, meningitis, locked-in syndrome, migraines, multiple sclerosis, myelopathy, or Tourette's syndrome.

13. The method of claim 1, wherein the administration of Compound (I) to the subject increases the expression of brain-derived neurotropic factor (BDNF) in the subject.

14. The method of claim 1, wherein the administration of Compound (I) to the subject increases the expression of glial cell line-derived neurotrophic factor (GDNF) in the subject.

15. The method of claim 1, wherein Compound (I), or a pharmaceutically acceptable salt or hydrate thereof, is formulated for oral administration.

16. The method of claim 15, wherein Compound (I), or a pharmaceutically acceptable salt or hydrate thereof, is formulated as a tablet.

17. The method of claim 1, wherein Compound (I) is a hydrochloride salt dihydrate.

18. The method of claim 1, wherein the therapeutically effective amount of Compound (I) is 0.1 mg/day to 1 g/day.

19. The method of claim 1, wherein the treating or diminishing of amblyopia in a subject results in improved vision in the subject's amblyopic eye.

20. The method of claim 1, wherein the subject developed amblyopia as a result of having one or more cataracts.

* * * * *

UNITED STATES PATENT AND TRADEMARK OFFICE
CERTIFICATE OF CORRECTION

PATENT NO. : 11,083,723 B2
APPLICATION NO. : 16/547164
DATED : August 10, 2021
INVENTOR(S) : Remy Henri Luthringer It is certified that error appears in the above-identified patent and that said Letters Patent is hereby corrected as shown below:

In the Claims

At Column 46, Claim number 8, Line numbers 54-55:
"wherein the subject is anisometric."

Should read:
-- wherein the subject is anisometropic. --

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*